United States Patent
Oblong et al.

(10) Patent No.: US 11,137,387 B2
(45) Date of Patent: Oct. 5, 2021

(54) METHOD OF IDENTIFYING OR EVALUATING SYNERGISTIC COMBINATIONS OF ACTIVES AND COMPOSITIONS CONTAINING THE SAME

(71) Applicant: The Procter & Gamble Company, Cincinnati, OH (US)

(72) Inventors: John Erich Oblong, Loveland, OH (US); Holly Ann Rovito, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1015 days.

(21) Appl. No.: 15/637,011

(22) Filed: Jun. 29, 2017

(65) Prior Publication Data

US 2017/0299577 A1    Oct. 19, 2017

Related U.S. Application Data

(63) Continuation of application No. 14/050,199, filed on Oct. 9, 2013, now Pat. No. 9,726,663.

(Continued)

(51) Int. Cl.
*G01N 33/00* (2006.01)
*G01N 33/50* (2006.01)
(Continued)

(52) U.S. Cl.
CPC ........... *G01N 33/5023* (2013.01); *A61K 8/22* (2013.01); *A61K 8/355* (2013.01); *A61K 8/675* (2013.01);
(Continued)

(58) Field of Classification Search
CPC .................................................. G01N 33/5023
(Continued)

(56) References Cited

U.S. PATENT DOCUMENTS 6,014,246 A   1/2000 Asher et al.
6,094,273 A   7/2000 Asher et al.
(Continued)

FOREIGN PATENT DOCUMENTS

EP       747042     12/1996
EP       841065      5/1998
(Continued)

OTHER PUBLICATIONS

Kang et al. "The Retinoid X Receptor Agonist 9-cis-retinoic Acid and the 24-hydroxylase Inhibitor Ketoconazole Increase Activity of 1,25-dihydroxyvitamin D3 in Human Skin in Vivo" J Invest Dermatol Apr. 1997; 108(4):513-8 (Year: 1997).*

(Continued)

*Primary Examiner* — Christine T Mui
*Assistant Examiner* — Emily R. Berkeley
(74) *Attorney, Agent, or Firm* — John G. Powell

(57) ABSTRACT

A method of identifying or evaluating synergistic combinations of actives such as skin-care actives that improve the metabolism of a cell and provides an advantage over using the actives alone. The method includes contacting cells with test agents, alone and in combination, and determining a response of the cells to the test agent(s), wherein the response corresponds to a change in a metabolic indicator associated with glycolysis and a change in a metabolic indicator associated with oxidative phosphylation.

7 Claims, 11 Drawing Sheets

Related U.S. Application Data

(60) Provisional application No. 61/711,521, filed on Oct. 9, 2012.

(51) Int. Cl.
*A61K 8/22* (2006.01)
*A61K 8/67* (2006.01)
*A61K 8/35* (2006.01)
*A61Q 19/00* (2006.01)
*A61Q 19/08* (2006.01)

(52) U.S. Cl.
CPC .............. *A61K 8/678* (2013.01); *A61Q 19/00* (2013.01); *A61Q 19/08* (2013.01); *G01N 33/5038* (2013.01); *A61K 2800/522* (2013.01); *A61K 2800/592* (2013.01)

(58) Field of Classification Search
USPC .............................................. 422/63; 436/63
See application file for complete search history.

(56) References Cited

U.S. PATENT DOCUMENTS

| | | | |
|---|---|---|---|
| 6,097,530 | A | 8/2000 | Asher et al. |
| 6,165,389 | A | 12/2000 | Asher et al. |
| 6,756,115 | B2 | 6/2004 | Fu et al. |
| 6,815,137 | B2 | 11/2004 | Hoshi et al. |
| 6,863,847 | B2 | 3/2005 | Fu et al. |
| 7,025,909 | B2 | 4/2006 | Fu et al. |
| 7,158,709 | B2 | 1/2007 | Hino |
| 7,695,737 | B2 | 4/2010 | Miyazaki et al. |
| 8,005,623 | B2 | 8/2011 | Hellerstein |
| 8,202,702 | B2 | 6/2012 | Neilson et al. |
| 8,633,191 | B2 | 1/2014 | Perry |
| 8,916,035 | B2 | 12/2014 | Frey et al. |
| 2001/0028890 | A1 | 10/2001 | Miyazaki et al. |
| 2003/0229141 | A1 | 12/2003 | Yu |
| 2004/0071965 | A1 | 4/2004 | Fu et al. |
| 2004/0106163 | A1* | 6/2004 | Workman, Jr. .... A61K 49/0021 435/14 |
| 2005/0238672 | A1 | 10/2005 | Nimni |
| 2008/0312169 | A1 | 12/2008 | Johnson et al. |
| 2009/0258841 | A1 | 10/2009 | Murphy et al. |
| 2010/0021697 | A1 | 1/2010 | Leyrer et al. |
| 2011/0105656 | A1 | 5/2011 | Sawada et al. |
| 2011/0243854 | A1 | 10/2011 | Wallace et al. |
| 2013/0095049 | A1 | 4/2013 | Castro Feo et al. |
| 2015/0316537 | A1 | 11/2015 | Oblong et al. |

FOREIGN PATENT DOCUMENTS

| | | |
|---|---|---|
| EP | 1238645 | 9/2002 |
| FR | 2851466 | 2/2003 |
| JP | 2002255987 | 9/2002 |
| JP | 2005-148573 A | 6/2005 |
| JP | 2008-298959 A | 12/2008 |
| WO | WO9603149 | 2/1996 |
| WO | WO9920271 | 4/1999 |
| WO | WO2001013956 | 8/2000 |
| WO | WO200269960 | 9/2002 |
| WO | WO2002078648 | 10/2002 |
| WO | WO2003007901 | 1/2003 |
| WO | WO2003092617 | 11/2003 |
| WO | WO2004035015 | 4/2004 |
| WO | WO2004037197 | 5/2004 |
| WO | WO2004082628 | 9/2004 |
| WO | WO2004089396 | 10/2004 |
| WO | WO2006097191 | 2/2006 |
| WO | WO2006097192 | 2/2006 |
| WO | WO2006097193 | 9/2006 |
| WO | WO2007002895 | 1/2007 |
| WO | WO2007113830 | 4/2007 |
| WO | WO2008003677 | 1/2008 |
| WO | WO2008046795 | 4/2008 |
| WO | WO2008141296 | 5/2008 |
| WO | WO2008156798 | 6/2008 |
| WO | WO2009062746 | 11/2008 |
| WO | WO2009108926 | 3/2009 |
| WO | WO2009132342 | 4/2009 |
| WO | WO2009087242 | 7/2009 |
| WO | WO2010026010 | 3/2010 |
| WO | WO2010039536 | 4/2010 |
| WO | WO2010121232 | 4/2010 |
| WO | WO2010059853 | 5/2010 |
| WO | WO2010132440 | 5/2010 |
| WO | WO2010065567 | 6/2010 |
| WO | WO2010139741 | 6/2010 |
| WO | WO2010141932 | 6/2010 |
| WO | WO2010150100 | 6/2010 |
| WO | WO2010085532 | 7/2010 |
| WO | WO2011075654 | 12/2010 |
| WO | WO2011031503 | 3/2011 |
| WO | WO2011038110 | 3/2011 |
| WO | WO2011109833 | 3/2011 |
| WO | WO2011119869 | 3/2011 |
| WO | WO2011150221 | 5/2011 |
| WO | WO2012009538 | 7/2011 |
| WO | WO2012016145 | 7/2011 |
| WO | WO2012040633 | 9/2011 |
| WO | WO2012040313 | 3/2012 |
| WO | WO2012075591 | 6/2012 |
| WO | WO 2014/059008 A1 | 4/2014 |

OTHER PUBLICATIONS

Ahmad, N. and Mukhtar, H. "Cytochrome P450: a target for drug development for skin diseases" J. Invest. Dermatol., 123: 417-425,2004.

Njar, V.C.et al. " Retinoic acid metabolism and blocking agents (RAM BAs) for treatment of cancer and dermatological diseases" Bioorganic& Medicinal Chemistry, 14: 4323-4340, 2006.

Kang, S., et al., "The retinoid X receptor agonist 9-cis retinoic acid and the 24-hydroxylase inhibitor ketoconazole increase the activity of 1,25-dihydroxyvitamin D3 in human skin in vivo" J. Invest. Dermatol., 108(4): 513-518, 1997.

Kang, S., et al. "Liarozole inhibits human epidermal retinoic acid 4-hydroxylase activity and differentially augments human skin responses to retinoic acid and retinol in vivo" J. Invest. Dermatol., 107(2): 183-187, 1996.

Van Wauweet al. "Liarozole, an inhibitor of retinoic acid metabolism, exerts retinoid-mimetic effects in vivo" J. Pharmacol. Exp. Ther., 261(2): 773-779, 1992.

Dockx, P., et al. "Inhibition of the metabolism of endogenous retinoic acid as treatment for severe psoriasis: an open study with oral liarozole". Br. J. Dermatol., 133(3): 426-432, 1995.

Miller, W.H., Jr. "The emerging role of retinoids and retinoic acid metabolism blocking agents in the treatment of cancer" Cancer,83(8): 1471-1482, 1998.

Lucker, G.P "Oral treatment of ichthyosis by the cytochrome p-450 inhibitor liarozole" Br. J. Dermatol., 136(1): 71-75, 1997.

Lucker, G.P.Het al. "Topical liarozole in ichthyosis: a double-blind, left-right comparative study followed by a long-term open maintenance study" Br. J. Dermatol., 565-595, 2005.

Reichrath, J. "Antimycotics: why are they effective in the treatment of seborrheic dermatitis?" Dermatology, 208:174-175, 2004.

McSorley, L.C. et al. "Identification of human cytochrome P450 isoforms that contribute to all-trans retinoic acid 4-hydroxylation" Biochemical Pharmacology, 60: 517-526, 2000.

Yengi, L.G., et al.. Quantitation of cytochrome P450 mRNA levels in human skin Anal. Biochem., 316: 103-110, 2003.

Svobodova, Alena, et al. "Attenuation of UVA-lnduced Damage to Human Keratinocytes by Silymarin", Journal of Dermatological Science (2007) 46, 21-30.

Mosby, C.V, Journal of the American Academy of Dermatology, vol. 60, No. 3, Mar. 1, 2009, p. AB29.

Rovito, H.A. Nicotimanide preferentially protects glycolysis in dermal fibroblasts under oxidative stress conditions British Journal of Dermatology, vol. 169, Jun. 21, 2013, pp. 15-24.

(56) References Cited

OTHER PUBLICATIONS

International Search Report PCT/US2013/064118, dated Oct. 9, 2013; 17 pages.
International Search Report, PCT/US2013/064116, dated Dec. 5, 2013, 11 pages.
Ferrick, David "Assay: Measurement of Mitochondrial Function: Extracellular Flux Assays Quantify Cellular Bioenergetics" Genetic Engineering & Biotechnology News; vol. 27, No. 19; Nov. 1, 2007, 4 pages.
Park, J. "Nicotinamide Prevents Ultraviolet Radiation-Induced Cellular Energy Loss" Photochemistry and Photobiology, 2010, 86:942-948.

* cited by examiner

METHOD OF IDENTIFYING OR EVALUATING SYNERGISTIC COMBINATIONS OF ACTIVES AND COMPOSITIONS CONTAINING THE SAME

FIELD OF THE INVENTION

The present invention is directed, generally, to a method of identifying or evaluating beneficial combinations of active ingredients for use in personal care compositions. More specifically, the present invention is directed to a method of identifying or evaluating synergistic combinations of actives that combat the effects of oxidative stress on skin cells.

BACKGROUND OF THE INVENTION

A fundamental basis for life is the need and ability of an organism to generate energy. In humans, food is taken in and converted into chemical compounds such as adenosine triphospate ("ATP") and nicotinamide adenine dinucleotide ("NAD"), which store the energy used by the cells of the body to perform the biological processes that sustain life. The metabolic pathways of the cells that convert the useful components of food (e.g., carbohydrates, fats and proteins) into usable energy are complex and may be affected by a variety of factors in ways that are not completely understood. Mammalian skin cells are no exception. Skin cells are known to include a variety of different kinds of cells that function together in a dynamic, complex relationship to maintain the health of the skin. For example, keratinocytes proliferate and differentiate to provide continuous skin turnover. Melanocytes are known to provide melanin synthesis for skin pigmentation. And fibroblasts are known for synthesizing the extracellular matrix and collagen, which helps maintain the skin's thickness and elasticity. Similarly, other cells found in or around the skin or other bodily organs, such as myocytes, stem cells, sebocytes, neurocytes, and adipocytes, all require energy derived from complex metabolic pathways, which can be undesirably impacted by a variety of different factors.

There is a growing awareness of the impact of various stressors on cellular bioenergetics and the impacts on cell aging, as well as other diseases (e.g., cancer, neurodegenerative diseases, diabetes, and cardiovascular disorders). One theory underlying some of these effects of altered metabolism in disease states is the Free Radical Theory of aging. Namely, that exposure of mammalian cells to reactive oxygen species ("ROS") causes damage to cellular structures and organelles such as the mitochondria. ROS are highly reactive molecules that contain oxygen (e.g., oxygen ions and peroxides). ROS are formed naturally within cells as a natural byproduct of the normal metabolism of oxygen and play a role in cell signaling and homeostasis. However, when a cell is exposed to a stressor such as heat or UV radiation, ROS levels can increase, and in some instances dramatically.

As the damage caused by ROS accumulates over time, it causes more and more oxidative stress at the cellular level that ultimately may lead to tissue damage and/or organ dysfunction. One effect of oxidative stress on cells is a diminished capacity of cellular bioenergetics, which can lead to reduced levels of ATP and/or NAD. This may be particularly problematic for human skin because the oxidative stress on human skin cells may manifest as visible signs of aging. Further, environmental stressors such as ultraviolet radiation ("UV") and pollutants (e.g., cigarette smoke, car exhaust, ozone) can lead to heightened levels of ROS production. Over time, this may result in noticeable changes in the skin's structure and morphology (e.g., "photodamage") and, to a more extreme degree, skin carcinomas.

Human skin cells defend against ROS by using redox regulators such as glutathione and NAD as well as various enzymes that can neutralize ROS. However, these defenses can be overwhelmed by the elevated spike from stressor-induced ROS, leading to not just acute but also chronic alterations in energy homeostasis and metabolism efficiencies, causing overall cellular dysfunction. To complicate matters, the variety of cells types associated with human skin and the complexity of the metabolic pathways of these cells makes it difficult to identify suitable compounds to help combat the anti-aging effect associated with exposure to a particular oxidative stressor or combination of stressors. Certain oxidative stressors affect different types of cells and/or metabolic pathways differently. This makes it difficult to select a suitable skin care active or combination of actives (whose affect may also vary depending on type of cell or metabolic pathway) that combat the undesirable affects of a particular stressor or stressors. While identifying actives that prevent, reduce and/or reverse the effects of oxidative stress on a cell is desirable, it is even more desirable to identify combinations of actives that act together to provide an advantage over using a single active. This is sometimes referred to as synergy. Identifying skin-care actives that work alone to combat the effects of oxidative stress can be difficult, but quickly and/or efficiently identifying skin-care actives that work in synergy can be formidable. Thus, there is a long felt need for a method of identifying synergistic combinations of skin-care actives that combat the undesirable metabolic effects associated with various oxidative stressors, especially common environmental stressors.

As an initial step in finding synergistic combinations of skin-care actives, a method capable of detecting the changes in cellular metabolism caused by stressors and actives must be identified. Various methods are known for evaluating the energy making processes of cells. For example, Clark-type electrode probes are known for measuring oxygen consumption. The Clark electrode provides kinetic information (i.e., rates of response) but introduces artifact (i.e., some undesirable and/or extraneous factor that influences the results of a test) by its continuous consumption of oxygen, presenting a decreasing oxygen pressure to the cells or isolated mitochondria in the measurement chamber. Although oxygen consumption may provide an indication of mitochondrial function, it only measures one component of cellular bioenergetics and does not provide an assessment of other metabolic pathways that contribute to bioenergetic equilibrium, namely glycolysis.

Another conventional method for assessing cellular energy production is by measuring the amount of ATP in a cell. Luminescent ATP assay kits are commercially available for quantifying total energy metabolism. ATP assays are known to be relatively sensitive but they may not be an ideal metric of mitochondrial function as cells strive to maintain a particular ATP budget and will adjust metabolism accordingly. Thus, alterations in ATP levels are usually only detectable during pathophysiological changes. In addition, ATP assays are destructive (i.e., the cells are destroyed in order to measure the amount of ATP) and they lack kinetic information. Further, artifact has been reported from residual ATP present in dying or dead cells. And like the Clark-electrode assay, ATP cannot determine the relative contribution of different metabolic pathways to total ATP yield.

Still another convention method for assessing cell energetics is with commercially available MTT/XTT or alamarBlue™ kits. While these kits may provide a relatively simple way to assess cell health, they are not as sensitive as ATP assays. In addition, they have been reported to introduce error through cell toxicity, the very parameter they are supposed to be measuring. Further, both assays are destructive and do not provide kinetic information.

Accordingly, it would be desirable to provide a method of identifying and/or evaluating beneficial combinations of actives that reduce, prevent and/or reverse the undesirable oxidative stress on skin cells. It would also be desirable to provide a skin care composition that includes skin-care actives identified by the foregoing method. It would further be desirable to provide a method of treating skin damaged by the oxidative stress effects of a particular stressor.

SUMMARY OF THE INVENTION

Figure 1A:
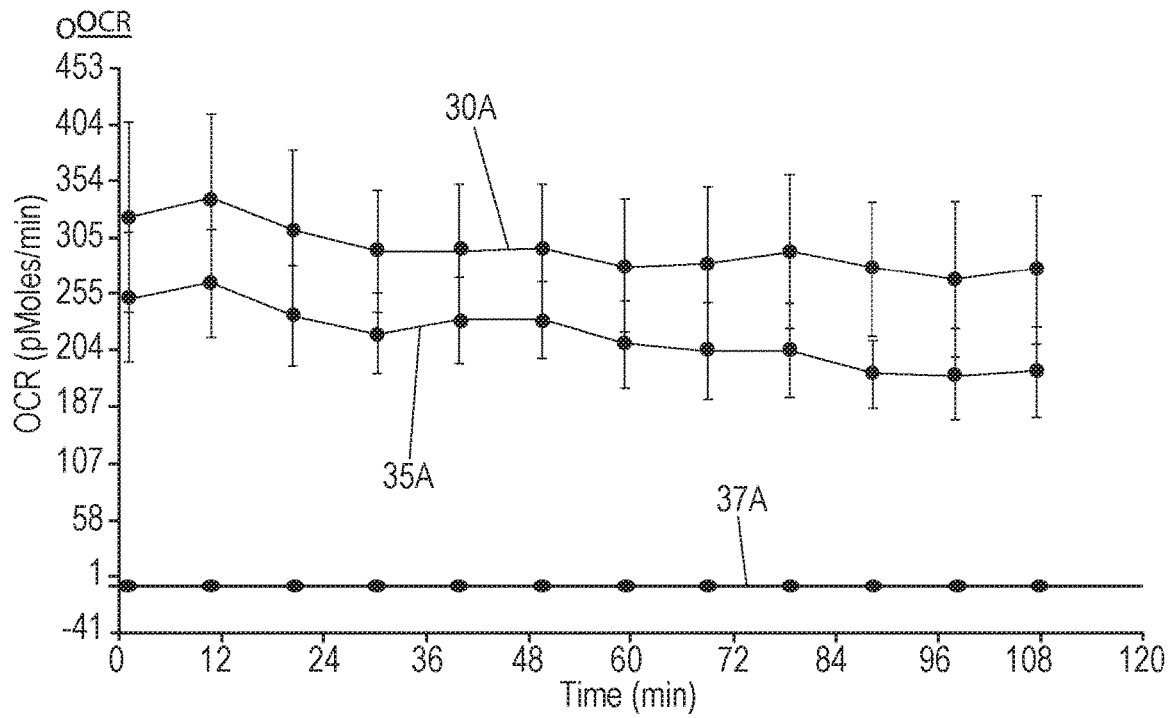
FIGS. 1A, 1B and 1C are illustrations of the oxygen consumption rate of keratinocytes.

Disclosed herein is a method of identifying or evaluating synergistic combinations of skin-care actives for use in a personal care composition. The method comprises contacting different populations of cells with different test agents, and then non-lethally detecting a metabolic indicator associated with glycolysis and oxidative phosphorylation from each population of cells. The metabolic indicator provides a response of each metabolic pathway to the test agents. By comparing the responses of a population to an individual test agent to the response to the test agents in combination, synergistic combinations of test agents can be identified.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

Definitions

"Additive effect" means that the effect provided by a combination of actives is equal to or substantially equal to the sum of their individual effects. For example, an additive effect would be demonstrated when a first active, which provides a 10% improvement in oxygen consumption rate when used alone, and a second active, which provides a 20% improvement in oxygen consumption rate when used alone, provide a 30% improvement to oxygen consumption rate when used in combination. A "more than additive effect," in this example, would be demonstrated when the combination of the first and second actives improves oxygen consumption rate by more than 30%.

"Cosmetic" means providing a desired visual effect on an area of the human body. The visual cosmetic effect may be temporary, semi-permanent, or permanent. Some non-limiting examples of "cosmetic products" include products that leave color on the face, such as foundation, mascara, concealers, eye liners, brow colors, eye shadows, blushers, lip sticks, lip balms, face powders, solid emulsion compact, and the like.

"Dermatologically acceptable" means that the compositions or components thereof being described are suitable for use in contact with human skin without undue toxicity, incompatibility, instability, allergic response, and the like.

"Different types of cells" means cells that differ from one another in their intended biological function. Examples of different types of cells, with respect to one another, include, without limitation, fibroblasts, keratinocytes, melanocytes, myoctyes, sebocytes and adipocytes.

"Disposed" means an element is positioned in a particular place relative to another element.

"Non-lethal," means that a test procedure in not intended to kill or destroy the cells being tested or observed. For example, non-lethally detecting a metabolic indicator means that at least 75% of the cells are viable after the detection (e.g., 80%, 85%, 90%, 95% or even up to 99% or more of the cells remain viable). Ideally, 100% of the cells are viable after a non-lethal test, but it is to be appreciated that the death or destruction of some cells may be unavoidable and/or unrelated to the test.

"Oxidative Stressor" means an environmental element that causes the formation of undesirable reactive oxygen species in a cell. Some non-limiting examples of oxidative stressors include ultraviolet radiation, cigarette smoke, ozone, engine exhaust, diesel exhaust, smog, surfactants, and radiation from a computer monitor or television.

"Personal-care composition" means a composition suitable for topical application on mammalian skin. The personal care compositions herein may be used in skin-care, cosmetic, and hair-care products; non-limiting uses of which include antiperspirants, deodorants, lotions (e.g. hand lotion and body lotion), skin-care products (e.g., face and neck lotions, serums, sprays), sunless tanners, cosmetics (e.g., foundation, concealer, blush, lipstick, lip gloss), depilatories, shampoos, conditioning shampoos, hair conditioners, hair dyes, body washes, moisturizing body washes, shower gels, skin cleansers, cleansing milks, hair and body washes, in-shower body moisturizers, pet shampoos, shaving preparations, after-shaves, razor moisturizing/lubricating strips, razor shave-gel bars, bar soaps, cleansing products, feminine-care products, oral-care products, and baby-care products. The methods of using any of the aforementioned compositions are also included within the meaning of personal-care composition.

"Regulate a skin condition" means maintaining skin appearance and/or feel with little to no degradation in appearance and/or feel.

"Safe and effective amount" means an amount of a compound or composition sufficient to significantly induce a positive benefit, preferably a positive skin or feel benefit, including independently or in combinations the benefits disclosed herein, but low enough to avoid serious side effects, i.e., to provide a reasonable benefit to risk ratio, within the scope of sound judgment of the skilled artisan.

"Skin" means the outermost protective covering of mammals that is composed of skin cells such as keratinocytes, fibroblasts and melanocytes. Skin includes an outer epidermal layer and an underlying dermal layer. Skin may also include hair and nails as well as other types of cells commonly associated with skin such as, for example, myocytes, Merkel cells, Langerhans cells, macrophages, stem cells, sebocytes, nerve cells and adipocytes.

"Skin-care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin. Some nonlimiting examples of "skin-care products" include skin creams, moisturizers, lotions, and body washes.

"Skin-care composition" means a composition that regulates and/or improves skin condition.

"Skin-care active" mean a compound or a combination of two or more compounds that, when applied to skin, provide an acute and/or chronic benefit to skin or a type of cell commonly found therein. Skin-care actives may regulate and/or improve skin or its associated cells (e.g., improve skin elasticity; improve skin hydration; improve skin condition; and improve cell metabolism).

"Synergy" and variations thereof mean that a combination of two or more actives improves the metabolism of a cell (e.g., glycolysis or oxidative phosphorylation) and provides an advantage (e.g., biological and/or economic) over using the actives alone. In some embodiments, synergy may be demonstrated by a combination of actives acting together to improve the metabolism of a cell beyond what the combination would normally be expected to provide. For example, if a combination of actives is expected to provide an additive effect, but instead provides a more than additive effect, the combination may be considered synergistic. Similarly, if a combination of actives is expected to provide a less than additive effect, but instead provide an additive effect, the combination may be considered synergistic. In some embodiments, synergy may be demonstrated by a combination of actives acting on different metabolic pathways (e.g., glycolysis and oxidative phosphorylation) to improve overall cell metabolism more than either active working alone. In some embodiments, synergy may be demonstrated by a combination of actives that each act on a different type of cell (e.g., keratinocytes and fibroblasts) to improve the metabolism of that type of cell, thereby improving the overall health of the skin. In some embodiments, synergy may be demonstrated by a combination of actives that do not inhibit one another with respect to improving the metabolism of a cell and/or metabolic pathway. In some embodiments, synergy may be demonstrated by a combination of actives wherein all the actives in the combination provide a metabolic benefit and at least one of the actives provides a non-metabolic benefit (e.g., economic, formulation, regulatory and/or safety benefit).

"Topical application" means to apply or spread the compositions of the present invention onto the surface of the keratinous tissue.

As humans age, damage from external and internal stressors on the cells of the body accumulates (i.e., oxidative stress), which may lead to decreased efficiency and function of tissue and organs. It is not uncommon for oxidative stress to manifest as a reduction in the ability of the cells to produce energy. Skin-care actives that reduce, stop or even reverse the effects of oxidative damage to skin are known. But identifying new and/or better skin-care actives is difficult due to the complexity of the metabolic pathways of a cell and/or the number of different types of cells found in skin. Surprisingly, it has been found that certain oxidative stressors impact the bioenergetics of certain types of skin cells in previously unappreciated ways. This new learning may be used to identify beneficial combinations of skin-care actives that combat the undesirable metabolic effects of oxidative stress on skin cells, which in turn may lead to improved skin-care compositions, more efficient methods of identifying combinations of actives and/or a more holistic approach to skin care. Accordingly, the novel method herein provides a convenient and accurate way to identify beneficial combinations of skin-care actives that act to combat the undesirable metabolic effects of oxidative stressors in ways that were previously unappreciated.

While some examples herein may be directed to skin cells such as keratinocytes and fibroblasts in conjunction with UV radiation, it is to be appreciated that the method may be adapted to great advantage for use with any type of cell in conjunction with any stressor, as desired.

Two key metabolic pathways for mammalian cells to produce energy are the oxidative phosphorylation ("oxphos") pathway and the glycolysis pathway. Both pathways are necessary to maintain a healthy energy balance within most mammalian cells. Oxidative phosphorylation involves the transfer of electrons from electron donors to electron acceptors such as oxygen in redox reactions, which results in the release of energy that is used to form ATP. In mammals, the redox reactions are carried out by a series of protein complexes within the mitochondria membrane, and the linked sets of proteins are called electron transport chains. The energy released by electrons flowing through this electron transport chain is used to transport protons across the mitochondrial membrane in a process called chemiosmosis, which generates potential energy in the form of a pH gradient and an electrical potential across this membrane. An enzyme commonly known as ATP synthase allows the potential energy to be used to generate ATP. Because the oxidative phosphorylation pathway uses oxygen to generate ATP, the rate at which a cell consumes oxygen may be used as a metabolic indicator of the cell. That is, the oxygen consumption rate of the cell may be directly correlated to energy production by the cell via oxidative phosphorylation. Additionally or alternatively, the carbon dioxide production rate may also be used as a metabolic indicator, since carbon dioxide is a by-product of cellular metabolism. A higher oxygen consumption rate or carbon dioxide production rate may indicate an increase in energy production from the oxidative phosphorylation pathway, and thus an improvement in the metabolism and/or health of a cell. Conversely, a lower oxygen consumption rate or carbon dioxide production rate may indicate a decrease in oxphos metabolism. As a result, it would desirable to identify and/or evaluate compounds that reduce, prevent and/or reverse the decrease in oxphos metabolism caused by oxidative stressors, especially common environmental stressors.

Glycolysis is the metabolic pathway that converts glucose into pyruvate. The free energy released in this process is used to form ATP and NADH (reduced NAD). Glycolysis is a definite sequence of ten reactions involving ten intermediate compounds (one of the steps involves two intermediates) that typically occurs in the cytosol of the cell. The intermediates provide entry points to glycolysis. For example, most monosaccharides such as fructose, glucose, and galactose, can be converted to one of these intermediates. The intermediates may also be directly useful. For example, the intermediate dihydroxyacetone phosphate (DHAP) is a source of the glycerol that combines with fatty acids to form fat. A by-product of glycolysis is lactic acid, which can form a lactate anion plus a proton in solution. Thus, lactic acid, lactate or proton concentration can be used as a metabolic indicator of glycolysis. That is, a change in extracellular pH or extracellular acidification rate may be directly correlated to energy production by the cell via the glycolysis pathway. A higher extracellular acidification rate may indicate an increase in energy production via the glycolysis pathway, and thus an improvement in the metabolism and/or health of a cell. Conversely, a lower extracellular acidification rate may indicate a decrease in glycolysis metabolism. As a result, it would desirable to identify and/or evaluate compounds that reduce, prevent and/or reverse the decrease in gycolysis metabolism caused by oxidative stressors, especially common environmental stressors.

Keratinocytes

Keratinoctyes are generally recognized as the predominant cell type in the epidermis, typically constituting about 95% of the cells found there. Keratinocytes are formed by differentiation from epidermal stem cells residing in the lower part of the stratum basale layer of the epidermis. Keratinocytes divide and differentiate as they move upward through the layers of the epidermis (e.g., stratum spinosum and stratum granulosum) to eventually become corneocytes in the stratum corneum. During the differentiation process, keratinocytes produce more and more keratin ("cornification") and eventually permanently withdraw from the cell cycle to form the corneocytes that make up the hard outer layer of the stratum corneum. Corneocytes are eventually shed off through desquamation as new cells come in. When oxidative stress reduces the metabolism of keratinocytes, the rate at which the keratinocytes divide and differentiate may be reduced or even halted. This, in turn, may reduce the rate at which lost corneocytes are replaced in the stratum corneum and ultimately lead to an undesirable decrease in the barrier properties of the skin. Thus, it may be desirable to identify synergistic combinations of skin-care actives that reduce, prevent and/or reverse the undesirable metabolic effects of oxidative stress from certain stressors (e.g., UV-A, UV-B, cigarette/tobacco smoke, smog, ozone, engine exhaust, volatile organic compounds) on keratinocytes.

It is well known that exposing skin to UV radiation can cause oxidative stress to skin cells. However, before now, it was not fully appreciated how particular types of skin cells react metabolically to different wavelengths of UV radiation, or how the metabolic reaction of a particular type of skin cell to UV radiation may change with time after exposure to the UV radiation. It has now been found that the oxphos and glycolysis metabolic pathways of keratinocytes respond differently to UV-B radiation (i.e., electromagnetic radiation in the wavelength range of 315-280 nm). In particular, it has been found that exposure of keratinocytes to UV-B radiation causes a decrease in metabolic activity in the oxphos pathway, but does not appear to have the same effect on the glycolysis pathway. Consequently, it may be desirable to identify synergistic combinations of skin-care actives that reduce, prevent and/or reverse the undesirable metabolic effects of UV-B radiation on keratinocytes. It may also be desirable to identify beneficial combinations of actives that reduce, prevent and/or reverse the undesirable metabolic effects of the same or different oxidative stressors and/or ROS on keratinocytes and at least one other type of cell commonly found in skin (e.g., fibroblasts, melanocytes, adipocytes, stem cells, sebocytes and neurocytes) to improve the overall health of the skin.

It has also been found that keratinocytes exhibit a previously unappreciated metabolic response to UV-B radiation at a particular dose and/or time after exposure. This discovery provides unique insight into screening for synergistic combination of skin-care actives to combat the effects of oxidative stress on keratinocytes from UV-B radiation. In particular, it is now known that between 5 milliJoules per square centimeter ("$mJ/cm^2$") and 50 $mJ/cm^2$ (e.g., from 7.5-40 $mJ/cm^2$, 10-30 $mJ/cm^2$, or even 15-30 $mJ/cm^2$) of UV-B radiation provides sufficient energy to induce a measurable metabolic response in the oxphos and/or glycolysis pathway of keratinocytes, but does not kill the keratinocytes. Further, in some instances it can be important to detect the desired metabolic indicator at least 1 hour after exposure of the keratinocytes to a stressor, but typically no more than 72 hours after exposure (e.g., from 2 to 24 hours; 3-23 hours; 4-22 hours; 5-21 hours; 6-20 hours; 7-19 hours; 8-18 hours; 9-17 hours; 10-16 hours; 11-15 hours; or even 12-14 hours). If the metabolic indicator is detected too soon, the cells may not have sufficient time to fully respond to the stressor. On the other hand, if too much time passes after exposure, a response may be missed (e.g., if the metabolism of the cell returns to the basal value). Further, it is now known that, in some instances, the kinetic data observed at particular times can provide important insights into the responses of keratinocytes to oxidative stressors and/or ROS, which may not be apparent when using a conventional static detection method (e.g., ATP assay).

In some instances, the method herein comprises exposing a plurality of keratinocytes to a stressor such as UV-B radiation and/or a ROS such as hydrogen peroxide and then contacting the keratinocytes with two or more test agents, alone and in combination. The metabolic responses of the keratinocyte to the stressor and test agents are obtained by detecting a metabolic indicator corresponding to each of the oxphos and glycolysis metabolic pathways. The metabolic responses are detected in real time in a controlled environment, and the oxphos and glycolysis indicators are obtained from the same cells at the same time. In some embodiments, it may be desirable to provide a basal value for each of the oxphos and glycolysis metabolic pathways of the keratinocyte and compare the metabolic responses to the basal value and/or each other to determine the response of the metabolic pathway to the stressor and/or test agents. "Basal value" means the value of the metabolic indicator at a normal resting state prior to exposure of the cell to a stressor or test agent. The basal value of a cell may be provided by measuring the metabolic indicators and/or by consulting the scientific literature and/or other suitable sources. However, measuring the basal value may be preferred since it is well known that the basal metabolic values of cells may vary due to a variety of environmental and intrinsic factors.

Figure 1B:
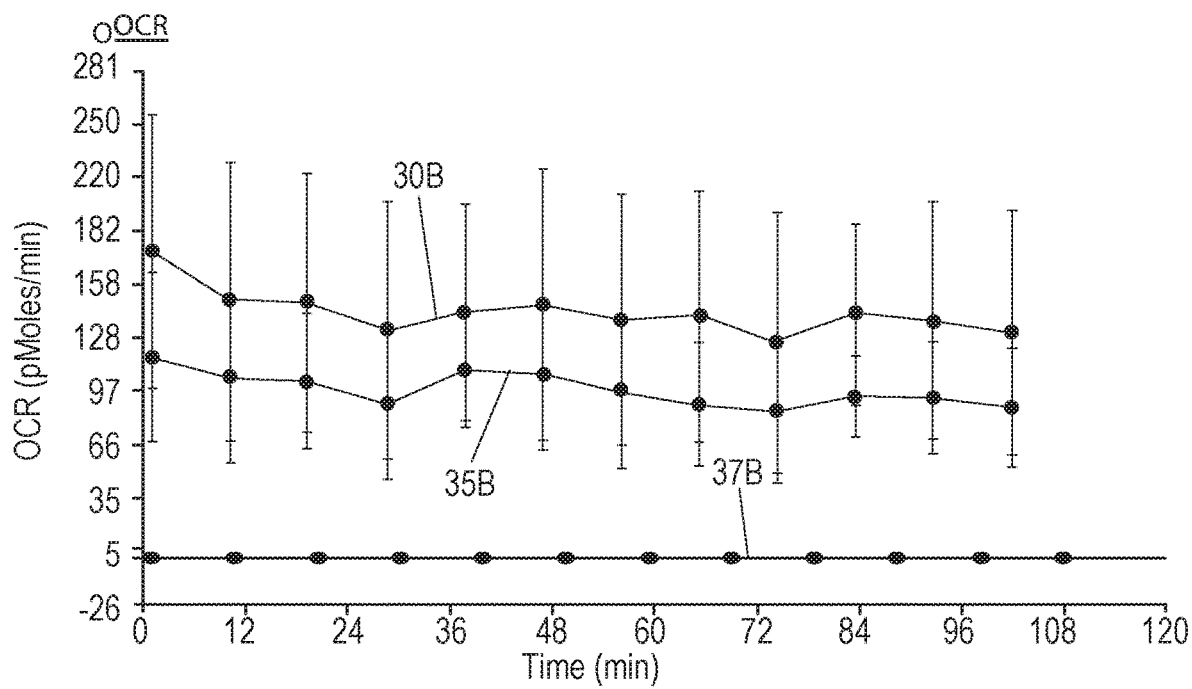
Figure 1C:
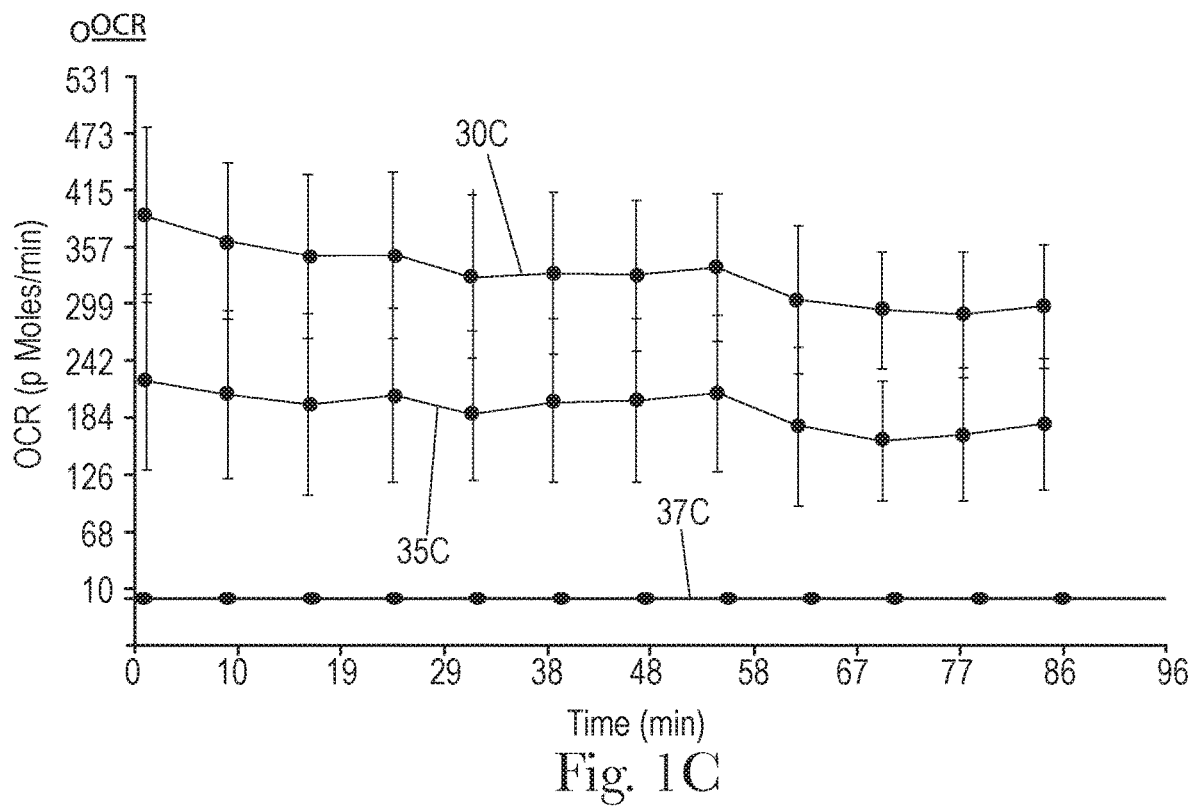

FIGS. 1A, 1B and 1C illustrate kinetic data obtained by detecting the oxygen consumption rate ("OCR") of keratinocytes after exposure to UV-B radiation (312 nanometers). The keratinocytes illustrated in the figures are primary keratinocytes obtained from Gibco Life Technologies, Grand Island, N.Y., USA. The cells were prepared and tested according to the method described in the Test Method below. The upper plots 30A, 30B and 30C in each of FIGS. 1A, 1B and 1C illustrate the basal OCR values of the keratinocytes (i.e., OCR with no UV-B exposure). The lower plots 35A, 35B and 35C of each of FIGS. 1A, 1B and 1C illustrate the response OCR values of the keratinocytes after exposure to UV-B radiation doses of 7.5, 15 and 30 $mJ/cm^2$, respectively. It is to be appreciated that providing the proper dose (i.e., 7.5, 15 or 30 $mJ/cm^2$) can depend on a variety of well-known factors (e.g., dose level desired, age of light bulb, type of light bulb, whether the instrument is warm), and it is well within the ability of one of ordinary skill to provide the desired dose of UV radiation. The control plots 37A, 37B and 37C illustrate the control OCR values measured on a well that did not contain any keratinocytes, but included the same medium as the other wells. The control values enable correction of the basal and/or response values for any background effect that may be present. The first data point in each plot is taken approximately one hour after exposure to UV-B radiation. As illustrated in FIGS. 1A, 1B and 1C, the response OCR values of the keratinocytes were generally lower than the corresponding basal OCR values. It is believed, without being limited by theory, that the data illustrated in FIGS. 1A, 1B and 1C indicate that UV-B radiation decreases the oxphos metabolism of keratinoctyes. Consequently, it would be desirable to identify synergistic combinations of skin-care actives that combat the undesirable effects of a stressor such as UV-B radiation on the oxphos metabolic pathway of keratinocytes, for example, by acting directly (i.e., cause an improvement even without the presence of a stressor or ROS) and/or indirectly (e.g., cause an improvement only when the cell is exposed a stressor or ROS) on the oxphos and/or glycolysis metabolic pathways of the keratinocytes and, optionally, another type of cell.

Figure 2:
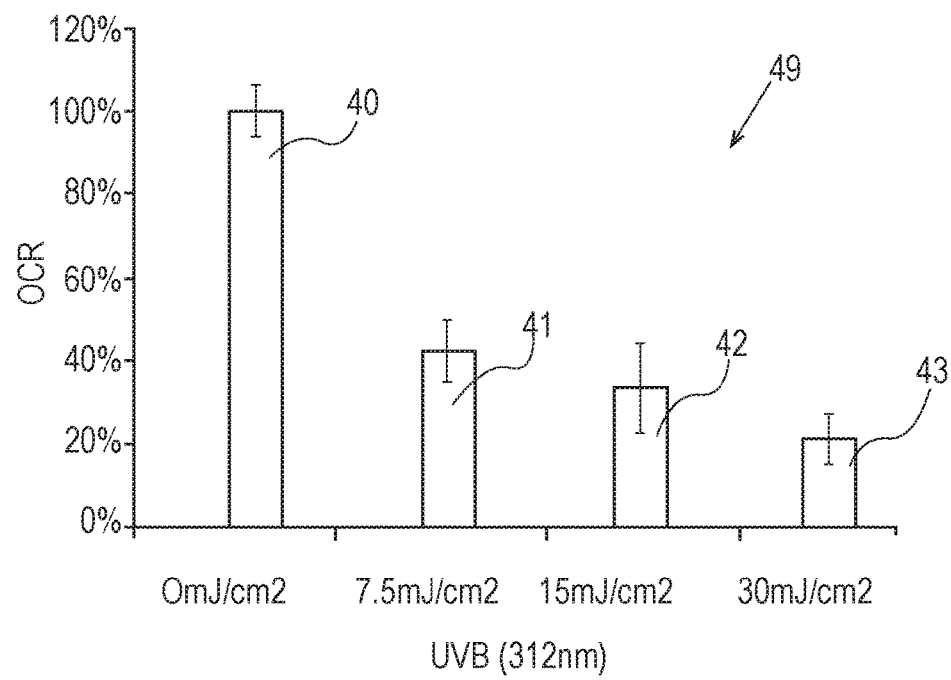
FIG. 2 is an illustration of the oxygen consumption rate of keratinocytes.

FIG. 2 illustrates the keratinocyte OCR response 24 hours after exposure to UV-B radiation (312 nanometers). The 24-hour values illustrated in FIG. 2 were obtained by exposing the keratinocytes to UV-B radiation and then incubating the plate at 37° C. and 5% $CO_2$ for 24 hours. Twenty-four hours after UV exposure, the cells were analyzed according to the method described below. The 24-hour basal value 40 is shown at the far left side of the chart 49. Immediately to the right of the basal value 40 is the 24-hour response OCR value 41 for a 7.5 $mJ/cm^2$ dose of UV-B radiation, followed by the 24-hour response OCR value 42 for a 15 $mJ/cm^2$ dose. And at the far right of the chart 49 is the 24-hour response OCR value 43 for a 30 $mJ/cm^2$ dose. As illustrated in FIG. 2, the keratinocytes continued to show a reduction in OCR 24 hours after exposure to UV-B doses of 7.5, 15 and 30 $mJ/cm^2$. Thus, it may be important to measure the keratinocyte oxphos response up to 24-hours or more (e.g., 48 or 72 hours) after exposure to UV-B, particularly when screening for synergistic combinations of skin-care actives that reduce, prevent and/or reverse the negative effects of UV-B on kertainocyte oxphos metabolism.

Figure 3A:
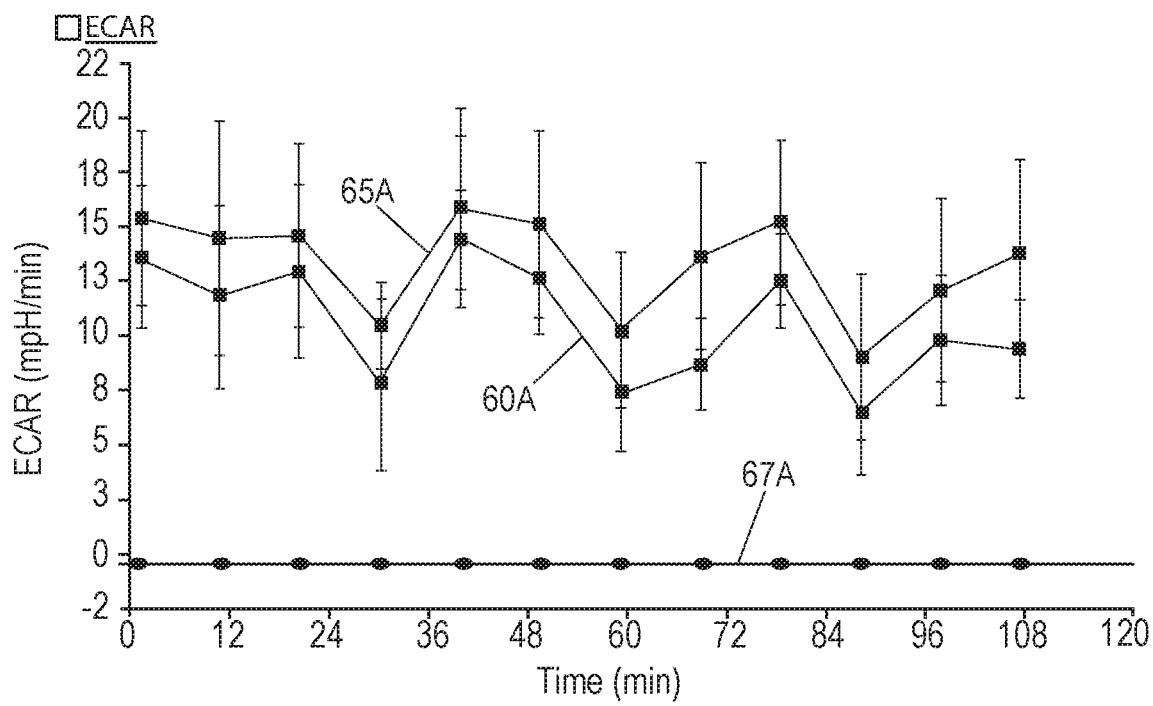
FIGS. 3A, 3B and 3C are illustrations of the extracellular acidification rate of keratinocytes.
Figure 3B:
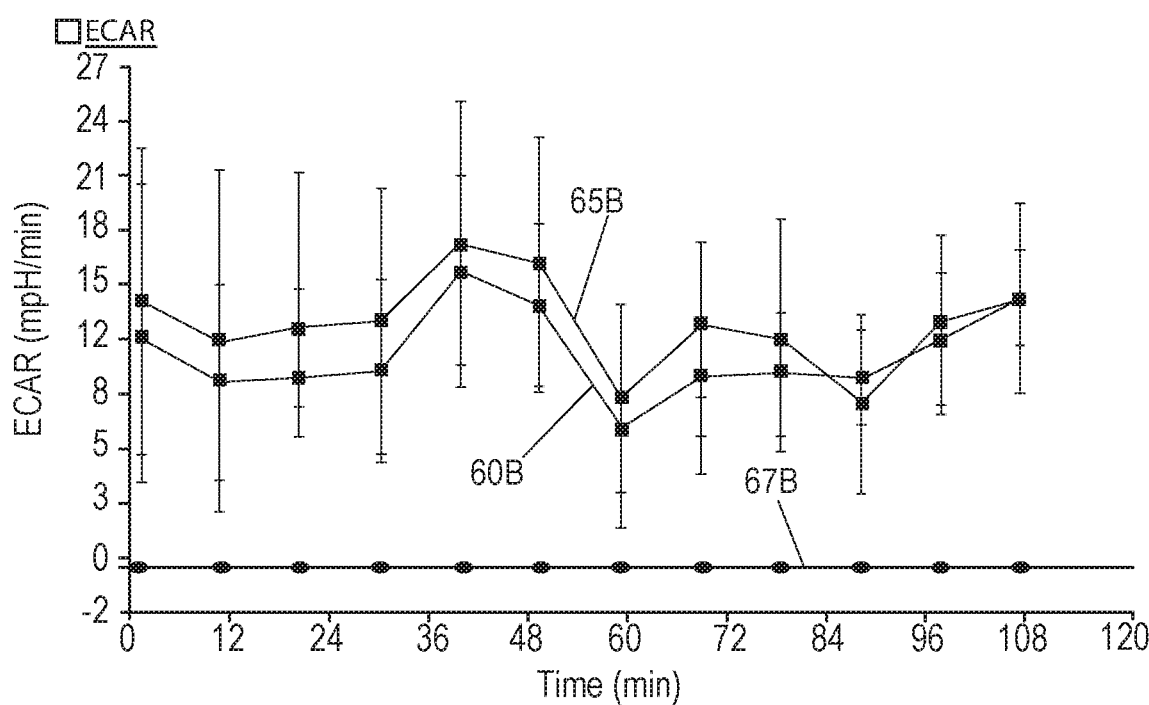
Figure 3C:
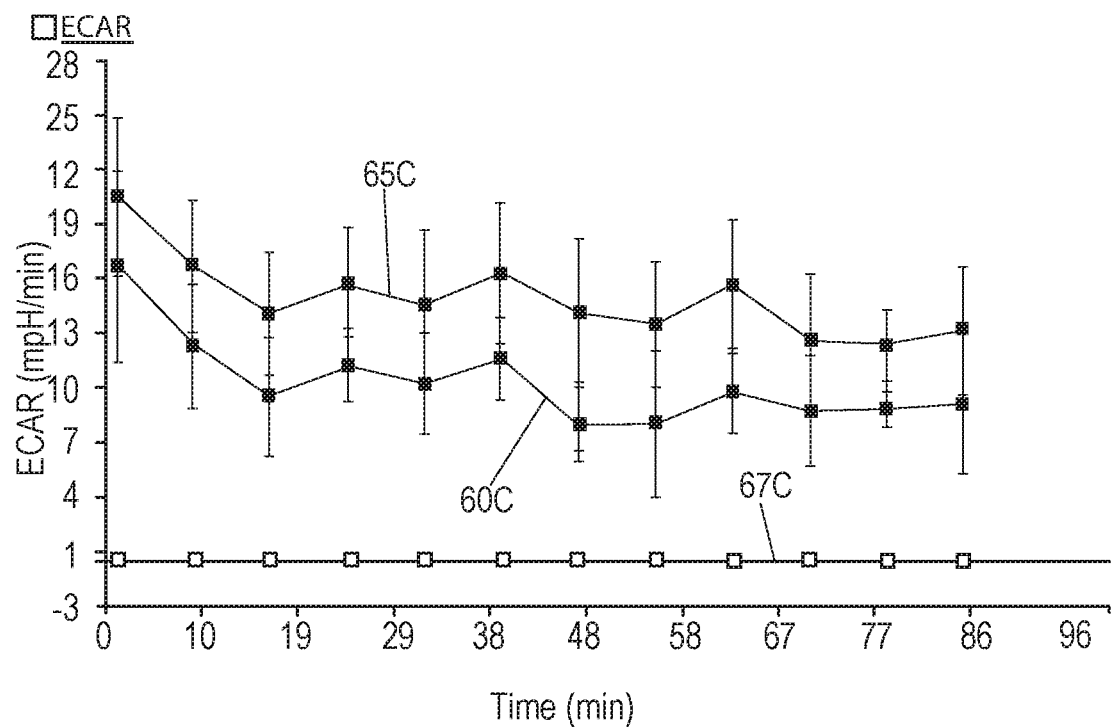

FIGS. 3A, 3B and 3C illustrate kinetic data obtained by detecting the extra cellular acidification rate ("ECAR") of keratinocytes after exposure to UV-B radiation (312 nanometers). The keratinocytes are primary keratinocytes obtained in the same way as described above with regard to FIGS. 1A, 1B and 1C, and the test was performed according to the method described in the Test Methods section below. The upper plots 65A, 65B and 65C in each of FIGS. 3A, 3B and 3C illustrate the response ECAR values of the keratinocytes after exposure to UV-B radiation doses of 7.5, 15 and 30 $mJ/cm^2$, respectively. The lower plot 60A, 60B and 60C illustrates the basal ECAR values of the keratinocytes (i.e., no UV-B exposure). The control plots 67A, 67B and 67C illustrate the control ECAR values measured on a well that did not contain any keratinocytes, but included the same medium as the other wells. As illustrated in FIGS. 3A, 3B and 3C, the control values 67A, 67B and 67C did not show any measurable change over time, whereas the response ECAR values of the keratinocytes were generally higher than the corresponding basal ECAR values. A statistical analysis of the ECAR response data was conducted using a 1-way analysis of variance ("ANOVA") with a Dunnett's correction, and the statistical analysis showed that the there was no statistically significant change in the ECAR response values 65A, 65B and 65C relative to the corresponding basal values 60A, 60B and 60C.

Figure 4:
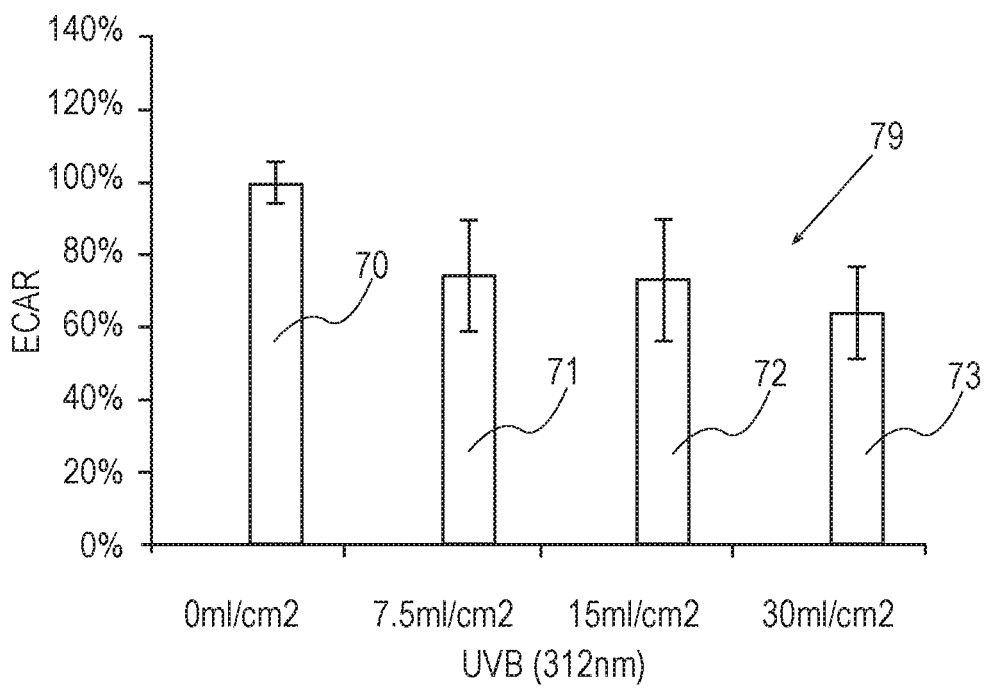
FIG. 4 is an illustration of the extracellular acidification rate of keratinocytes.
Figure 5A:
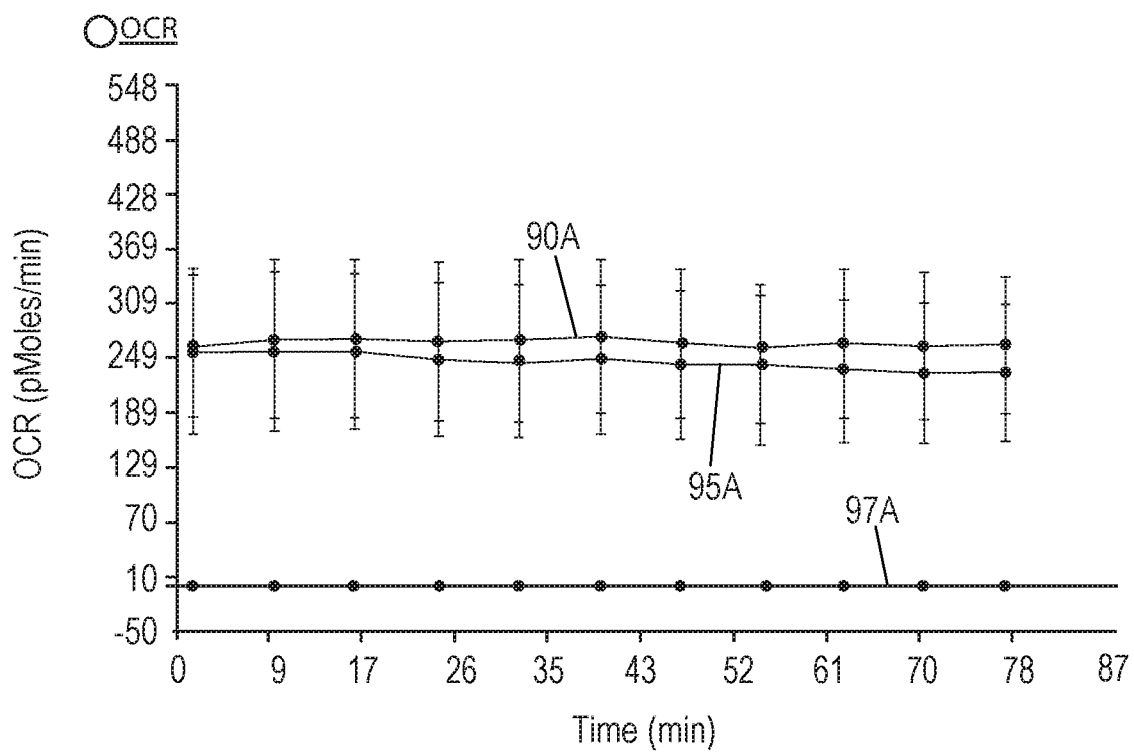
FIGS. 5A, 5B, 5C, 5D and 5E are illustrations of the oxygen consumption rate of fibroblasts.
Figure 5B:
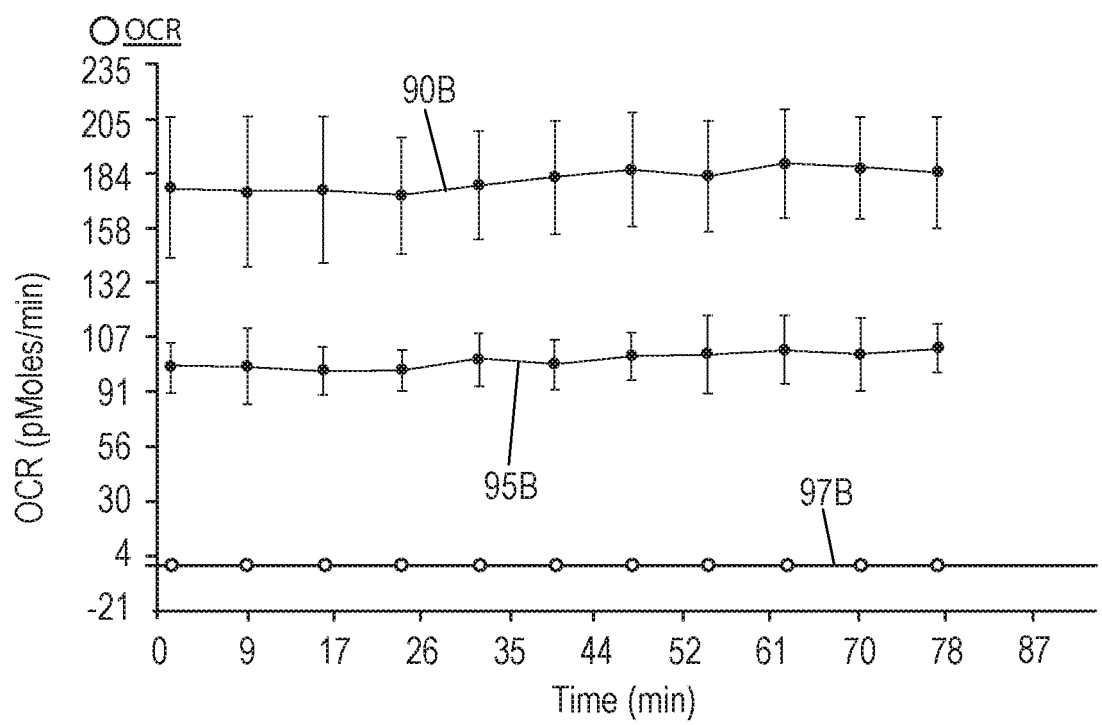
Figure 5C:
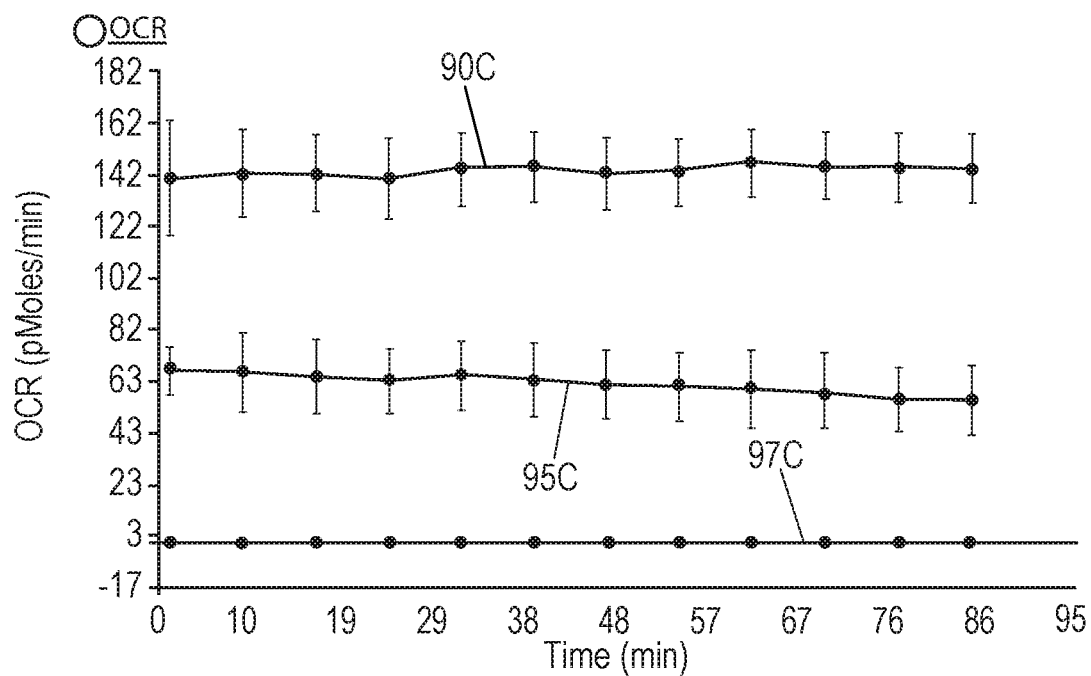
Figure 5D:
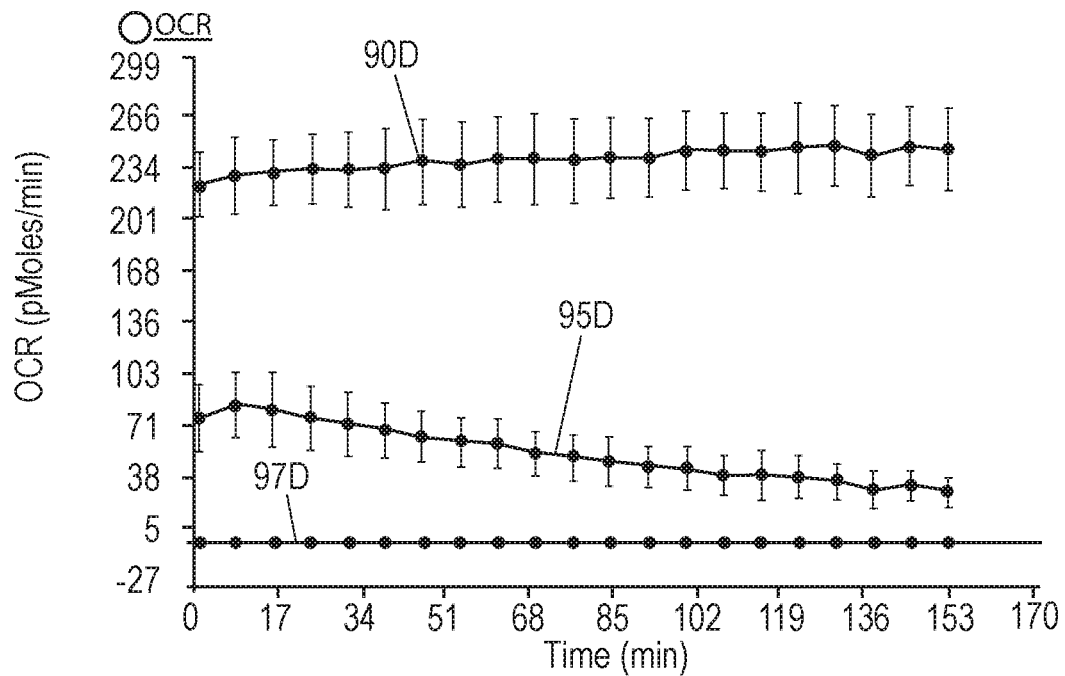
Figure 5E:
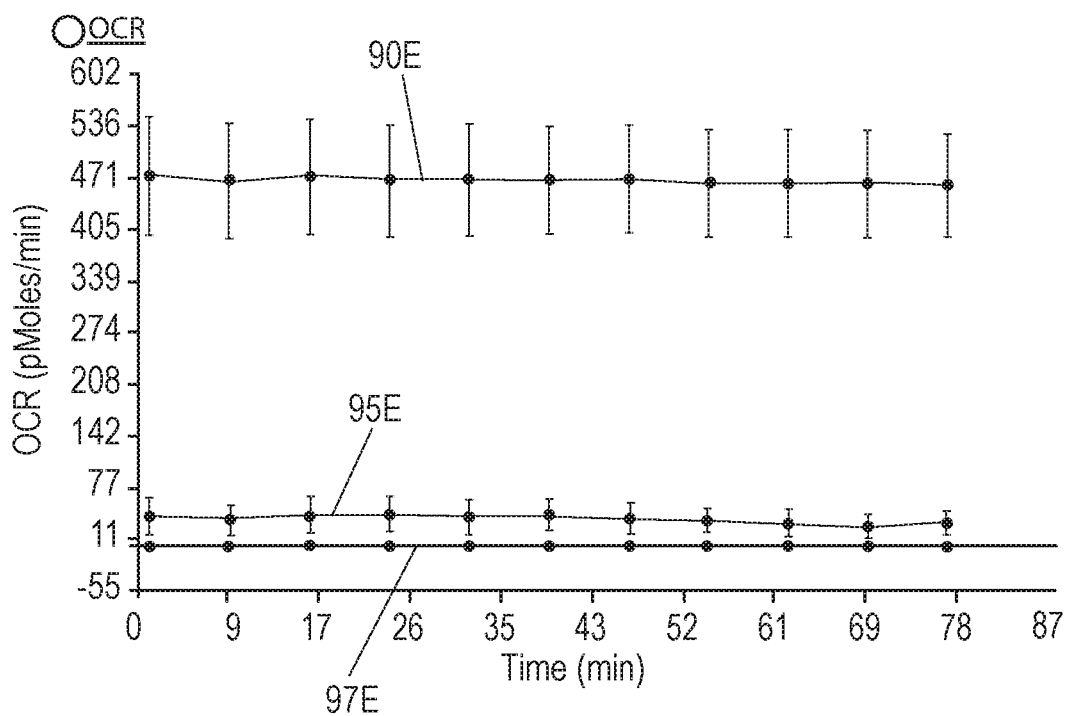

FIG. 4 illustrates the keratinocyte ECAR response 24 hours after exposure to UV-B radiation (312 nanometers). The 24-hour values illustrated in FIG. 4 were obtained by exposing the keratinocytes to UV-B radiation and then incubating the plate at 37° C. and 5% $CO_2$ for 24 hours. Twenty-four hours after UV exposure, the cells were analyzed according to the method described below. The 24-hour basal ECAR value 70 is shown at the far left side of the chart 79. Immediately to the right of the basal value 70 is the 24-hour response ECAR value 71 for a 7.5 $mJ/cm^2$ dose of UV-B radiation, followed by the 24-hour response ECAR value 72 for a 15 $mJ/cm^2$ dose. And at the far right of the chart 79 is the 24-hour response ECAR value 73 for a 30 $mJ/cm^2$ dose. A statistical analysis of the 24-hour ECAR response data was conducted using a 1-way ANOVA with a Dunnett's correction. The analysis indicated that the there was a statistically significant change in the ECAR response values relative to the basal value. Thus, the amount of time that passes after exposure of keratinocytes to a stressor such as UV-B radiation may be an important factor to consider when screening for synergistic combinations of skin-care actives that reduce, prevent and/or reverse the negative effects of UV-B on kertainocyte glycolysis metabolism. In particular, it may be desirable to wait more than 2 hours after exposure to as stressor such UV-B radiation (e.g., 4, 6, 8, 10, 12, 14, 16, 18, 20, 24, 48, or 72 hours) to detect a metabolic indicator of glycolysis in keratinocytes.

Fibroblasts

In some instances, it may be desirable to identify synergistic combinations of skin-care actives that reduce, prevent and/or reverse the undesirable effects of oxidative stress from certain stressors on fibroblasts and, optionally, other types of cells commonly found in skin. Fibroblasts are found in the dermal layer of the skin and the hypodermal (i.e., sub-cutaneous) layer, and are generally recognized as the cells that synthesize the extracellular matrix ("ECM") and collagen to provide the structural framework for the tissues of mammals. The ECM and collagen help cushion the body from stress and strain by providing tensile strength and elasticity to the skin. Fibroblasts also play an important role in wound healing. When oxidative stress reduces the metabolism of fibroblasts, the body's ability to synthesize collagen and the ECM may be reduced resulting in saggy, thinner looking skin. And the ability of the body to heal wounds may be impeded.

As mentioned previously, it has not been fully appreciated how particular types of skin cells react metabolically to different wavelengths of UV radiation, or that the metabolic reaction of a particular type of skin cell to UV radiation may change with time after exposure to the UV radiation. This adds uncertainty and difficulty to a process of identifying suitable skin-care actives. Surprisingly, it has been found that the oxphos and glycolysis metabolic pathways of fibroblasts respond differently to UV-A radiation. While most of the UV-B radiation that contacts the skin is absorbed or reflected by the keratinocytes, longer wavelength UV-A radiation can penetrate through the epidermis and damage the underlying fibroblasts and other cells commonly found in the dermis and hypodermis. In particular, it has been found that exposure of fibroblasts to UV-A radiation that exceeds a threshold energy level causes a decrease in metabolic activity in the oxphos pathway. Exposure of fibroblasts to UV-A radiation also may result in a decrease in metabolic activity in the glycolysis pathway. In addition, both metabolic pathways may exhibit changes in their responses at different energy levels and times after exposure. This discovery provides unique insight important for identifying synergistic combinations skin-care actives that combat the effects of oxidative stressors such as UV-A on fibroblasts. For example, it is now known that between 1 and 50 Joules per square centimeter ("$J/cm^2$") of UV-A radiation may provide sufficient energy to induce a measurable metabolic response in the oxphos and/or glycolysis pathway, but does not generally kill the fibroblasts. Suitable ranges of UV-A radiation include between 5 and 40, 10 and 30, or even about 20 $J/cm^2$. Further, it also now known that in some instances it can be important to detect the metabolic indicator at least 1 hour after exposure of the fibroblasts to a stressor, but typically not more than 24 hours after exposure (e.g., from 2 to 24 hours; 3-23 hours; 4-22 hours; 5-21 hours; 6-20 hours; 7-19 hours; 8-18 hours; 9-17 hours; 10-16 hours; 11-15 hours; or 12-14 hours). If the metabolic indicator is detected too soon, the cells may not have sufficient time to fully respond to the stressor. On the other hand, if too much time elapses, an important transient response to the stressor may not be detected. Further, it is now known that, in some instances, the kinetic data observed at particular times can provide important insights into the responses of fibroblasts to oxidative stressors and/or ROS, which may not be apparent when using a conventional static detection method (e.g., ATP assay).

In some embodiments, the method herein includes exposing a plurality of fibroblasts to a stressor such as UV-A radiation and/or an ROS such as hydrogen peroxide and then contacting the fibroblasts with two or more test agents alone and in combination. The metabolic responses of the fibroblasts to the stressor and/or the test agents may be obtained by detecting a metabolic indicator corresponding to each of the oxphos and glycolysis metabolic pathways. The metabolic responses are detected in real time in a controlled environment, and the oxphos and glycolysis indicators are obtained from the same cells at the same time. In some embodiments, it may be desirable to provide a basal value for at least one of the oxphos and glycolysis metabolic pathways of the fibroblasts, and compare the metabolic responses to the basal value and/or each other to determine the response of the metabolic pathway to the stressor and/or test agent.

FIGS. 5A, 5B, 5C, 5D and 5E illustrate the kinetic data obtained by detecting the oxygen consumption rate of fibroblasts after exposure to UV-A radiation (365 nm). The fibroblasts are dermal fibroblasts obtained from ATCC, Bethesda, Md. (BJ cell line). The cells were prepared and tested according to the method described in more detail below. The upper plots 90A, 90B, 90C, 90D and 90E in each of FIGS. 5A, 5B, 5C, 5D and 5E illustrate the basal OCR values of the fibroblasts (i.e., the OCR with no UV-A exposure). The lower plots 95A, 95B, 95C, 95D and 95E of each of FIGS. 5A, 5B, 5C, 5D and 5E illustrate the response OCR values of the fibroblasts after exposure to UV-A radiation doses of 1, 5, 10, 20 and 30 $J/cm^2$, respectively. The control plots 97A, 97B, 97C, 97D and 97E illustrate the control OCR values measured on wells that did not contain any fibroblasts, but included the same medium as the other wells. The control value enables correction of the basal values and response values for any background effect that may be present. As illustrated in FIGS. 7A 5A, 5B, 5C, 5D and 5E, the response OCR values of the fibroblasts were generally lower than the corresponding basal OCR values. Thus, it is believed, without being limited by theory, that the data illustrated in FIGS. 5A, 5B, 5C, 5D and 5E indicate that UV-A radiation, at doses of greater than 1 $J/cm^2$, may decrease the oxphos metabolism of fibroblasts. Consequently, it would be desirable to identify synergistic combinations of skin-care actives that combat the undesirable effects of a stressor such as UV-A radiation on the oxphos metabolic pathway of fibroblasts, for example, by acting directly (i.e., cause an improvement even without the presence of a stressor or ROS) and/or indirectly (e.g., cause an improvement only when the cell is exposed a stressor or ROS) on the oxphos and/or glycolysis metabolic pathways of the fibroblasts and, optionally, another type of cell.

Figure 6:
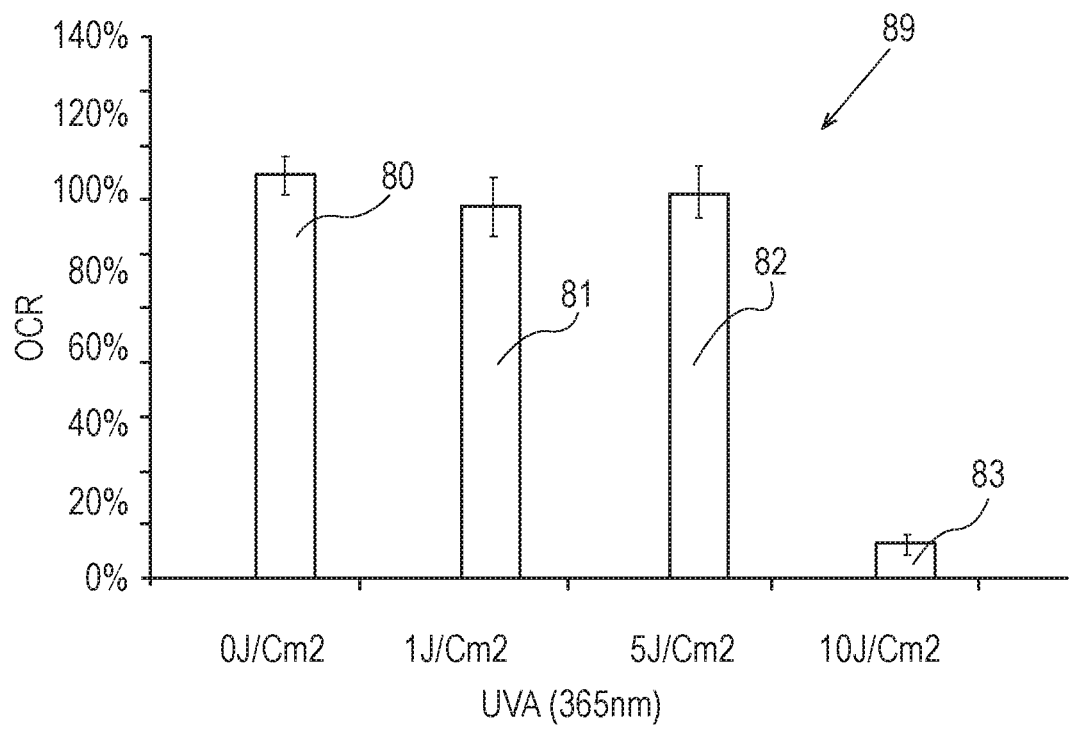
FIG. 6 is an illustration of the oxygen consumption rate of fibroblasts.

FIG. 6 illustrates fibroblast OCR responses at 24 hours after exposure to UV-A radiation (365 nm). The 24-hour values illustrated in FIG. 6 were obtained by exposing the fibroblasts to UV-A radiation and then incubating the plate at 37° C. and 5% $CO_2$ for 24 hours. Twenty-four hours after exposure to UV-A, the cells were analyzed according to the method described below. The 24-hour basal OCR value 80 is shown at the far left side of the chart 89. Immediately to the right of the basal value 80 is the 24-hour response OCR value 81 for a 1 $J/cm^2$ dose of UV-A radiation, followed by the 24-hour response OCR value 82 for a 5 $J/cm^2$ dose. And at the far right of the chart 89 is the 24-hour response OCR value 83 for a 10 $J/cm^2$ dose. As illustrated in FIG. 6, the fibroblasts appear to show a reduction in OCR after 24 hours only at a dose of 10 $J/cm^2$. Thus, it may be important to measure the fibroblast oxphos response up to 24-hours or more (e.g., 48 or 72 hours) after exposure to UV-A radiation when screening for synergistic combinations of skin-care actives that combat the undesirable effects of UV-A at a dose of, for example, greater than 5 $J/cm^2$ or 10 $J/cm^2$. However, when screening for synergistic combinations of skin-care actives that combat the undesirable metabolic effects of UV-A radiation on fibroblasts at doses of less than 10 $J/cm^2$ or 5 $J/cm^2$, time and resource consuming steps in the screening process may be avoided by not testing at the lower doses.

Figure 7A:
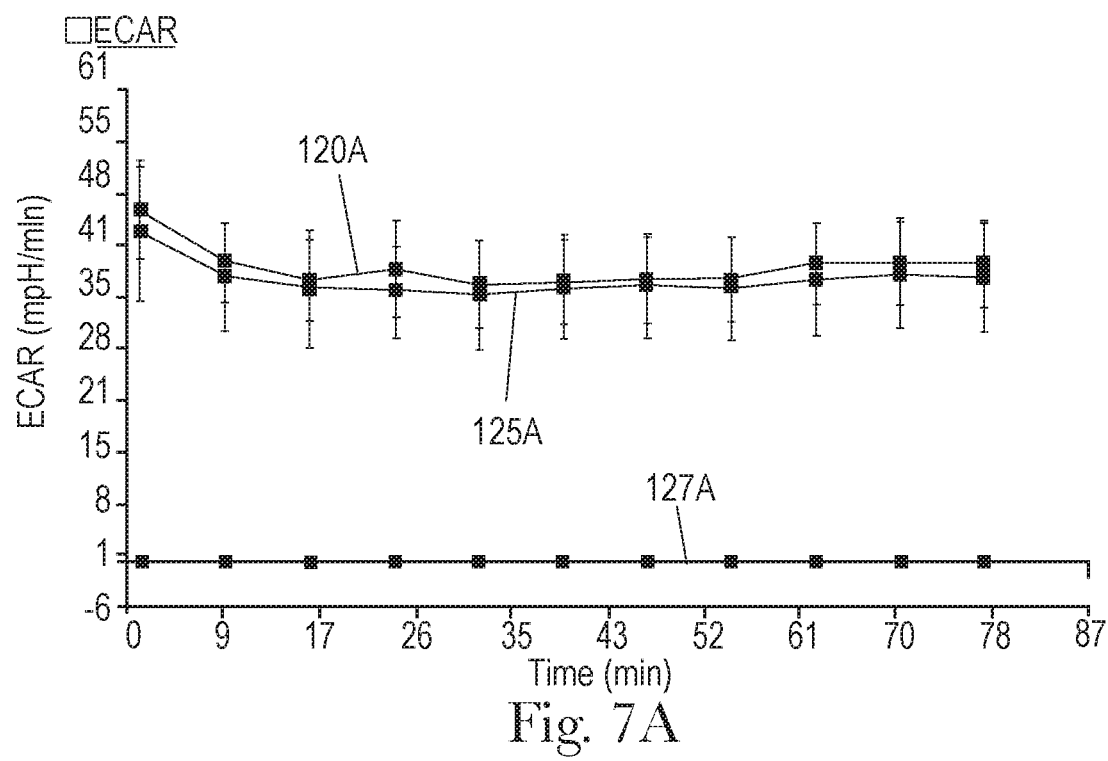
FIGS. 7A, 7B, 7C, 7D and 7E are illustrations of the extracellular acidification rate of fibroblasts.
Figure 7B:
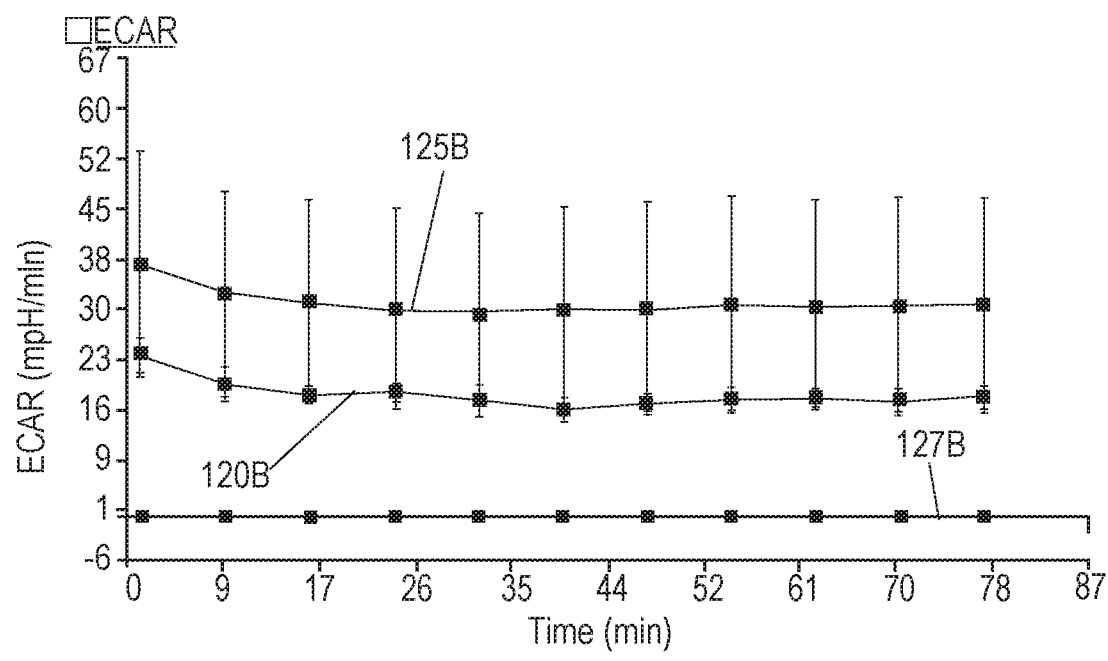
Figure 7C:
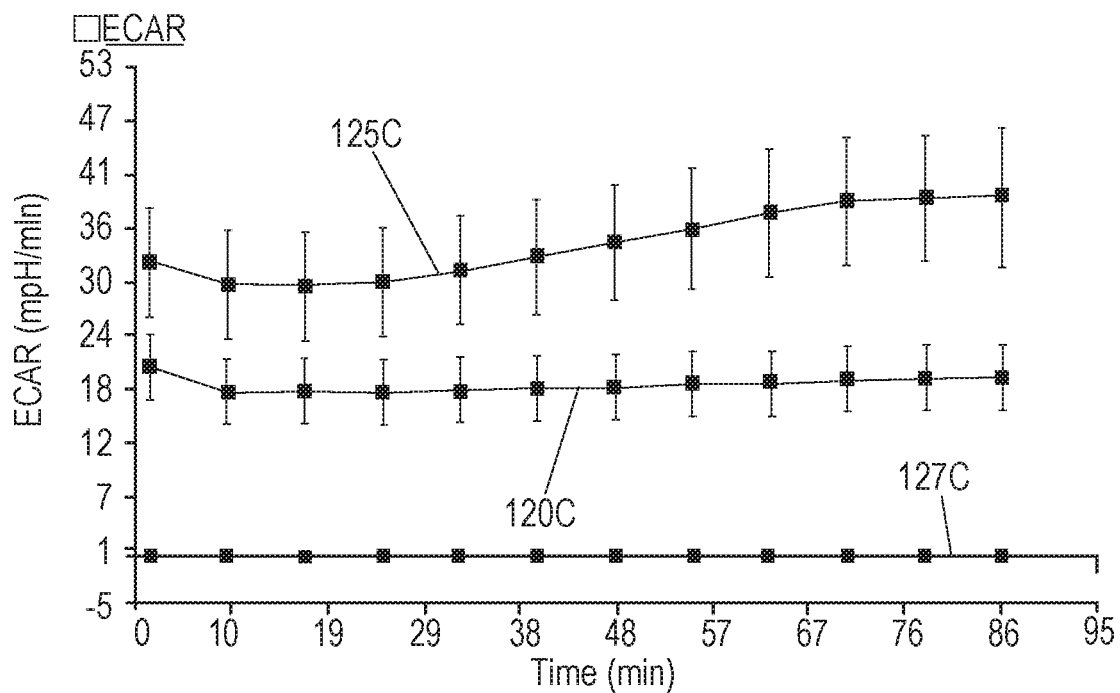
Figure 7D:
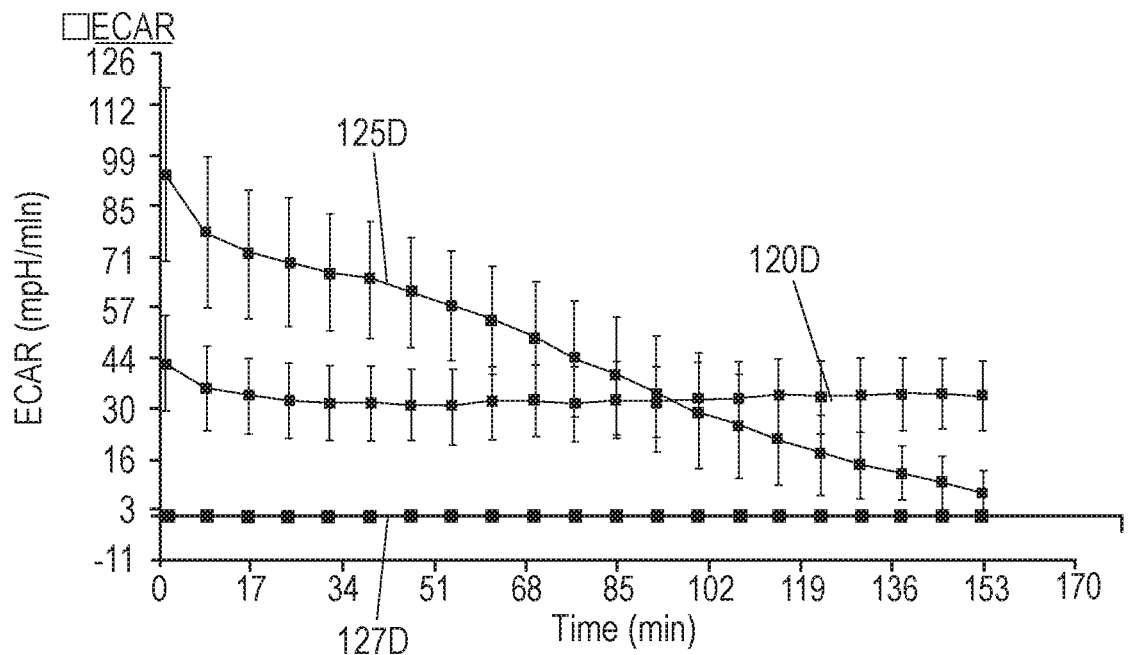
Figure 7E:
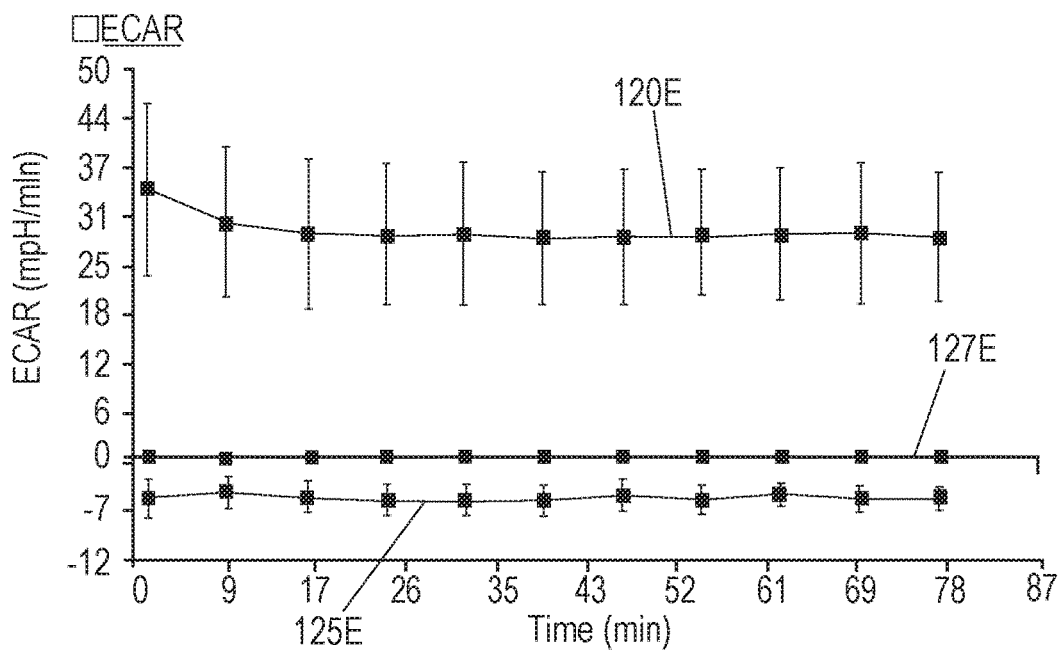

FIGS. 7A, 7B, 7C, 7D and 7E illustrate the kinetic data obtained by detecting the extra cellular acidification rate of fibroblasts. The fibroblasts are obtained in the same way as described above with regard to FIGS. 7A, 7B, 7C, 7D and 7E, and the test was performed according to the method described in the Test Methods section below. In FIGS. 7A, 7B, 7C, 7D and 7E the basal ECAR values are represented by plots 120A, 120B, 120C, 120D and 120E; the response ECAR values are represented by plots 125A, 125B, 125C, 125D and 125E; and the control ECAR values are represented by plots 127A, 127B, 127C, 127D and 127E. The basal values 120A, 120B, 120C, 120D and 120E and control values 127A, 127B, 127C, 127D and 127E are obtained in the same way as described above. The response ECAR values 125A, 125B, 125C, 125D and 125E correspond to the responses of the fibroblasts after exposure to 1, 5, 10, 20 or 30 $J/cm^2$ of UV-A radiation (365 nm), respectively. As can be seen in FIG. 7A, the response ECAR value 125A of the fibroblasts after exposure to 1 $J/cm^2$ of UV-A was generally about the same as the basal value 120A, which may indicate that the glycolysis metabolic pathway of the fibroblast is relatively unaffected at this dose. But as illustrated in FIGS. 7B and 7C, the response ECAR values 125B and 125C of the fibroblasts after exposure to 5 and 10 $J/cm^2$ of UV-A, respectively, were higher than the corresponding basal values 120B and 120C. Surprisingly, when the fibroblasts were exposed to 20 $J/cm^2$ of UV-A, as illustrated in FIG. 7D, the response ECAR value 125D started out higher than the basal value 120D, but appears to decrease until eventually (i.e., approximately 85 to 102 minutes) crossing over the basal value 120D line to end up lower than the basal value 120D. The response ECAR value 125E of the fibroblasts after exposure to 30 J/cm2 is substantially lower than the basal value, which may indicate that the glycolysis metabolic pathway of the fibroblasts has completely shut down. Thus, it is believed, without being limited by theory, that the data illustrated in FIGS. 7A, 7B, 7C, 7D and 7E indicate that both the time after exposure and dose are important factors to consider when providing a suitable way to identify synergistic combinations of skin-care actives that combat the effects of UV-A radiation on fibroblast glycolysis. In particular, doses above and below 20 $J/cm^2$ may have very different effects on the glycolysis metabolism of fibroblasts, and appreciating these differences can help identify beneficial combinations of skin-care actives that combat the undesirable effects of UV-A without inhibiting the desirable effects.

Figure 8:
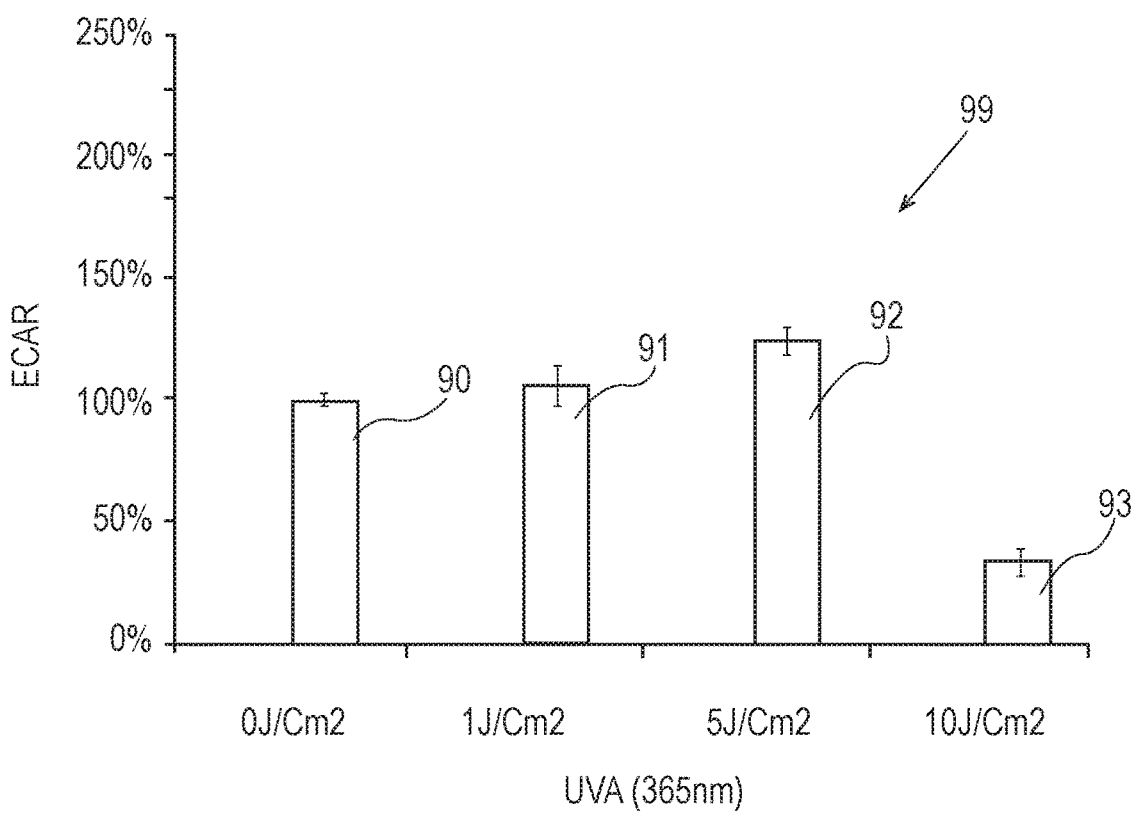
FIG. 8 is an illustration of the extracellular acidification rate of fibroblasts.

FIG. 8 illustrates fibroblast ECAR responses at 24 hours after exposure to UV-A radiation (365 nm). The 24-hour values illustrated in FIG. 8 were obtained by exposing the fibroblasts to UV-A radiation and then incubating the plate at 37° C. and 5% $CO_2$ for 24 hours. Twenty-four hours after exposure to UV-A, the cells were analyzed according to the Test Methods below. The 24-hour basal ECAR value 90 is shown at the far left side of the chart 99. Immediately to the right of the basal value 90 is the 24-hour response ECAR value 91 for a 1 $J/cm^2$ dose of UV-A radiation followed by the 24-hour response ECAR value 92 for a 5 $J/cm^2$ dose. And at the far right of the chart 99 is the 24-hour response ECAR value 93 for a 10 $J/cm^2$ dose. As illustrated in FIG. 8, the fibroblasts appear to show a reduction in ECAR after 24 hours only at a dose of 10 $J/cm^2$. Thus, the time after exposure, especially up to 24 hours, may be an important factor to consider when screening for synergistic combinations of skin-care actives that combat effects of UV-A radiation on fibroblast glycolysis, depending on the dose of UV-A.

Personal Care Compositions and Method of Using the Same

Because of the skin health and/or appearance benefit provided by a healthy skin cells, it may be desirable to incorporate a synergistic combination of two or more skin-care actives identified according to the method herein into a cosmetic composition. That is, it may be desirable to include the skin-care actives as ingredients in the cosmetic composition. Such cosmetic compositions may include a dermatologically acceptable carrier and a synergistic combination of skin-care actives that reduce, prevent and/or reverse the undesirable metabolic effects of oxidative stress on keratinocytes, fibroblasts and/or other types of cells commonly found in skin (e.g., melanocytes, myocytes, stem cells, sebocytes, neurocytes, and adipocytes). In a particularly suitable example, the composition may contain a safe and effective amount of niacinamide and tocoquinone. In this example, the niacinamide may be added at between 0.001% and 20% (e.g., 0.1-10% or 0.5-5%) and the tocoquinone may be added at between 0.0001% and 20% (e.g., 0.01-10%, 0.1%-5%, or 0.5%-3%). It may be desirable to add a combination of niacinamide and tocoquinone sufficient to improve the oxphos and glycolysis metabolic pathways of fibroblasts exposed to hydrogen peroxide relative to using niacinamide and tocoquinone alone.

In some embodiments, the synergistic combination of skin-care actives may comprise two or more skin-care actives acting together to provide more than a predicted benefit. For example, a first and second active may each act on one or both of the oxphos and glycolysis pathways to provide an increase in overall cellular metabolism that exceeds the expected additive effect of the actives. In this example, a first active may provide an improvement to the oxphos pathway of a keratinocyte when used alone, whereas a second active appears to provide no benefit to the oxphos pathway when used alone. However, when used in combination, the first and second actives improve oxphos metabolism more than when either is used alone. In another example, a first active may improve the oxphos metabolism of a fibroblast while a second active improves the glycolysis metabolism of the fibroblast. Continuing with this example, the first and second actives when used in combination improve oxphos and glycolysis metabolism, thereby improving the overall metabolism of the fibroblast. In still another example, a first active may act to combat the undesirable metabolic effects of a particular stressor on glycolysis while the second active acts to combat the undesirable metabolic effects of the same stressor on oxphos, thereby reducing, preventing and/or reversing the undesirable effect of the stressor on overall cellular metabolism more than when either active is used alone.

In some embodiments, a synergistic combination of skin-care active may comprise two or more skin-care actives that act on different types of skin cells to provide an improvement to the overall health of the skin. For example, first and second actives that act on the oxphos and/or glycolysis pathway of a different type of cell (e.g., keratinocytes and fibroblasts) may be incorporated into a skin-care composition to provide a holistic skin-care benefit. In this example, the first active may improve the oxphos pathway of keratinocytes leading to an improvement in the barrier properties of skin, while the second active improves the glycolysis metabolism of fibroblasts leading to an improvement in skin thickness and/or elasticity.

In some embodiments, the synergistic combination may be two or more skin-care actives that do not inhibit one another with respect to improving the metabolism of a cell and/or metabolic pathway. For example, a first active may be added to improve oxphos metabolism and a second active may be added to improve glycolysis metabolism. In this example, neither active inhibits the respective metabolic benefit provided by the other active. This type of synergistic combination is important because some skin-care actives that may work well when used alone may not provide the same kind or amount of metabolic improvement when used together, which is undesirable. In another example, a first and second active may both provide an improvement in oxphos metabolism, which can be the same or different (i.e., one active improves metabolism better than the other when the actives are used alone), one of the actives also provides a non-metabolic benefit (e.g., economic or safety) over the other active. For example, one of the actives may be easier to source, cheaper to purchase, easier to formulate, have regulatory approval in a particular country or region that the other does not and/or have less and/or no undesirable side effects at higher concentrations. Thus, the first and second actives may be used in a synergistic combination to provide a desired level of metabolic benefit and a desired level of non-metabolic benefit.

The cosmetic compositions herein may include one or more optional ingredients of the kind commonly included in the particular cosmetic compositing being provided. For example, the cosmetic composition may include additional skin-care actives known for regulating and/or improving the condition of mammalian skin. Nonlimiting examples of such optional ingredients include emollients, humectants, vitamins; peptides; and sugar amines. Other optional ingredients include sunscreen actives (or sunscreen agents) and/or ultraviolet light absorbers. In certain embodiments, the cosmetic composition may include a colorant, a surfactant, a film-forming composition, and/or a rheology modifier. Suitable cosmetic compositions herein may be in any one of a variety of forms known in the art, including, for example, an emulsion, lotion, milk, liquid, solid, cream, gel, mouse, ointment, paste, serum, stick, spray, tonic, aerosol, foam, pencil, and the like. The cosmetic compositions may also be incorporated into shave prep products, including, for example, gels, foams, lotions, and creams, and include both aerosol and non-aerosol versions. Other cosmetic compositions include antiperspirant, deodorant, and personal cleaning compositions such as soap and shampoo. Nonlimiting examples of cosmetic compositions and optional ingredients suitable for use therein are described in U.S. Publication No. 2010/0239510 filed by Ha, et al., on Jan. 21, 2010.

Compositions incorporating skin-care actives identified by the novel methods described herein may be generally prepared according to conventional methods known in the art of making compositions and topical compositions. Such methods typically involve mixing of ingredients in one or more steps to a relatively uniform state, with or without heating, cooling, application of vacuum, and the like. For example, emulsions may be prepared by first mixing the aqueous phase materials separately from the fatty phase materials and then combining the two phases as appropriate to yield the desired continuous phase. In certain embodiments, the compositions may be prepared to provide suitable stability (physical stability, chemical stability, photostability, etc.) and/or delivery of active materials. The composition may be provided in a package sized to store a sufficient amount of the composition for a treatment period. The size, shape, and design of the package may vary widely. Some package examples are described in U.S. Pat. Nos. D570,707; D391,162; D516,436; D535,191; D542,660; D547,193; D547,661; D558,591; D563,221; and U.S. Publication Nos. 2009/0017080; 2007/0205226; and 2007/0040306.

The personal care compositions disclosed herein may be applied to the skin at an amount and frequency to improve skin elasticity, improve hydration, regulate or improve skin condition, maintain or improve the signs of skin aging, or maintain or improve insult-affected keratinous tissue. For example, it may be desirable to identify a target area of skin in need of a skin-care benefit applying a cosmetically safe and effective amount of the personal care composition to the target area. In some instances, the skin-care composition may be used as a specialized treatment for an entire face, with concentrated usage in areas with expression lines, wrinkles, undesirable tone or spots. Further, the personal-care compositions herein may be used to produce a chronic and/or acute skin or cosmetic benefit by topically applying to the skin of a mammal in need of such treatment a safe and effective amount of the skin-care composition.

Test Method

This method enables the non-lethal, simultaneous detection of metabolic indicators associated with the oxidative phosphorylation and glycolysis metabolic pathways in a controlled environment. The method also enables the collection of kinetic data. When assessing the metabolic response to a stressor, test agent or combination of test agents, it is important to assess both metabolic pathways simultaneously to understand how the two metabolic pathways interact with the stressor or test agent(s) and/or to one another. Additionally, it is important to monitor the metabolic pathways in real time (i.e., repeating periodic measurements) to observe trends and/or transient responses that may be missed when using methods that provide only static data. Thus, destructive tests are not suitable for use herein since they typically only allow for a single measurement.

It is also important to detect the metabolic indicator in a controlled environment to reduce the likelihood of artifact introduction. A suitable controlled environment should minimize or prevent any undesirable influence by external environmental conditions (e.g., temperature, pressure, humidity, light, and contact by undesirable gaseous, liquid and/or solid contaminants). For example, if the metabolic indicator being detected is oxygen consumption rate and the test sample is open to the environment, the measured oxygen concentration may not accurately reflect the amount of oxygen consumed by the cells, since at least some of the consumed oxygen may be replaced by environmental oxygen. Additionally, the test method itself should not introduce artifact into the measurement. For example, it is known that the Clark Electrode consumes oxygen, which is the very thing it is supposed to detect. Thus, the oxygen concentration measured by a Clark Electrode device may not accurately reflect the amount of oxygen consumed by the cells in the test.

It is to be appreciated that environmental changes such as a change in the temperature of the medium may result in unwanted measurement errors. In particular, the capacity of the media to hold dissolved gasses changes with temperature, and therefore may result in an apparent change in dissolved gas concentration as the media seeks equilibrium with the surrounding environment. Further, the measurement properties of at least some types of sensors may change with temperature. Accordingly, it may be particularly desirable to control the environmental conditions such as the temperature of the medium in the test vessel and/or surrounding environment or apply a correction factor to the measurement. Similarly, any evaporation from the media due to other uncontrolled environmental conditions such as humidity or exposure to air currents may artificially impact the measurements made from various sensors including those of dissolved gases, ions, and temperature. Thus, providing a controlled environment to minimize or eliminate these factors can be important.

In some instances, the device used to detect the metabolic parameters may include a stage adapted to receive and support a test vessel (e.g., multiwell microplate). The device may also include a plunger configured to receive a barrier for isolating the environment within the test vessel from the external environment. The barrier may be configured to mechanically cooperate with a portion of the test vessel to seal the opening in the test vessel, for example, by mating with a seat or step in the test vessel wall. Additionally or alternatively, the plunger and barrier may be configured to reduce and/or expand the volume of the test vessel and the volume of the medium within the test vessel including at least a portion of the cells (e.g., 5-50%). For example, the barrier may be inserted into and/or retracted out of the test vessel by relative movement of the stage and the plunger. In some embodiments, the method may include perfusing additional media through the vessel and/or replenishing the medium. Reducing the volume of the medium enables the temporary creation of a highly concentrated volume of cells within a larger volume of cell media to improve the ability of the sensor(s) to detect sensitive changes in metabolic indicators in the medium that result from biological activity of the cells. By temporarily, rather than permanently, reducing the media volume (and therefore concentrating the cell/media mixture), cells are exposed to a non-normal environment for only a brief period of time, and therefore may not be adversely affected (e.g., killed) by the measurement process.

The instrument should also include a sensor capable of analyzing the desired metabolic indicator(s). In some embodiments, the sensor may be disposed on the barrier and/or plunger. The sensor should be in sensing communication with the medium and configured to detect the desired metabolic indicator. The sensor may be configured to sense the presence and/or the concentration of the metabolic indicator; sense a rate of change of a concentration of the metabolic indicator; and/or sense a first concentration of a first metabolic indicator, sense a second concentration of a second metabolic indicator, and determine a relationship between the first concentration and the second concentration. It may be desirable to configure the sensor to detect the metabolic parameter without disturbing the cells. The instrument may also include a computer programmed to automate one or more aspects of the tests, including data collection and recording, cycling through one or more test steps and transferring a test agent or stressor to the extracellular environment. In some embodiments, the sensor may be coupled to the computer.

Suitable nonlimiting examples of devices that provide a controlled environment; non-lethal and simultaneous detection of metabolic indicators; and kintetic data are disclosed in U.S. Pat. Nos. 7,276,351; 7,638,321; and 7,851,201, to Teich et al.; and U.S. Pat. No. 8,202,702 to Neilson, et al. A particularly suitable device is the XF Extracellular Flux Analyzer available from Seahorse Bioscience, Massachusetts.

Cell Culture and Sample Preparation

Cells to be tested according to the method herein may be obtained by any suitable means known in the art. For example, the cells may be isolated from a natural environment (e.g., the skin of a person) or purchased from a suitable commercial source. The cells may be a primary cell line (i.e., a cell line that is isolated from a biological tissue source and propagated under normal tissue culture conditions) or an immortalized cell line (i.e., a cell line that has been modified via chemical or genetic modification such that its proliferation and doubling index are significantly greater than that available from primary cell lines). In some embodiments, frozen primary or immortalized cell lines may be obtained from a suitable commercial source and diluted with an appropriate growth medium into tissue culture flasks (e.g., collagen coated T-75 flask available from BD Biosciences) for incubation (e.g., at 37° C.). Once the cells are ready for testing, they may be placed in a suitable test vessel (e.g., multi-well vessels, single-well vessels, one or more tubes, and conventional test plates such as a 12-well plate, 24-well plate, 96-well plate or the like). A test medium may be provided in the test vessel to form an extracellular environment. The test medium should keep the cells alive and healthy for at least the duration of the test (e.g., at least 4 hours, 8 hours, 12 hours, 24 hours, 48 hours, 72 hours). The number of cells in each well should be sufficient to obtain a suitable measurement (e.g., $4 \times 10^4$ for keratinocytes and $1 \times 10^5$ for fibroblasts). It is to be appreciated that during testing the cells may be suspended in the test medium, attached to a suitable substrate disposed in the test vessel and/or attached to the test vessel.

By way of example, the keratinocytes discussed above with regard to FIGS. 1A, 1B, 1C, 2, 3A, 3B, 3C and 4 are frozen, human primary keratinoctyes obtained from Gibco Life Sciences. The keratinocytes were grown to 70-80% confluence in EpiLife® brand keratinoyte medium (available from Invitrogen, Grand Island, N.Y.) supplemented with human keratinocyte growth supplement and gentamicin/amphotericin B×500 solution, both available from Invitrogen. For each test, two separate donors of keratinocytes were cultured and equal cell numbers of each donor were combined in the test vessel. In this example, $2 \times 10^4$ keratinocytes from each donor were placed in a Gelatin-coated, 24-well plate, for a total of approximately $4 \times 10^4$ keratinocytes in each well. The number of cells present may be determined by any suitable means known in the art (e.g., using a Coulter counter). The keratinocytes were placed in the Gelatin-coated plates 24 hours prior to testing and 100 μL of the keratinocyte medium described above was added to each well. A test medium was made by modifying a commercially available EpiLife® medium that is devoid of buffers, calcium, glucose, pyruvate, and glutamine. The EpiLife® medium was modified by adding 10 ng/ml Insulin; 10 ng/ml Hydrocortisone; 60 μM Calcium Chloride; 10 mM of Glucose; 1 mM of Pyruvate; and 2 mM of Glutamine. The test medium was warmed to 37° C. and the pH adjusted to 7.4 with sodium hydroxide. The keratinocyte medium in the wells was replaced by the test medium 1 hour prior to taking measurements With regard to the fibroblasts discussed above in FIGS. 5A, 5B, 5C, 5D, 5E, 6, 7A, 7B, 7C, 7D, 7E and 8 frozen, human dermal fibroblasts were obtained from the BJ cell line commercially available from ATCC, Bethesda, Md. The fibroblasts were grown to 70-80% confluence in a fibroblast culture medium of Eagle's Minimum Essential Medium ("EMEM") supplemented with 10% fetal bovine serum ("FBS") and gentamicin/amphotericin B×500 solution (EMEM and FBS are available from ATCC and gentamicin/amphotericin B×500 solution is available from Invitrogen). The fibroblasts were plated at $1 \times 10^5$ per well in Gelatin-coated plates 24 hours prior to testing. Each well included 100 μL of the fibroblast medium described above. A test medium was made from Dulbecco's Modified Eagle Medium (available from Seahorse Bioscience), 25 mM Glucose and 1 mM pyruvate. The test medium was warmed to 37° C. and the pH adjusted to 7.4. The cells were grown and plated at 37° C. and 5% $CO_2$ air. The fibroblast medium in the wells was replaced by the test medium 1 hour prior to taking measurements.

The Gelatin-coated plates may be prepared by coating each well in a multi-well plate (e.g., 24-well or 96-well plates available from Seahorse Biosciences, Massachusetts) with 0.2% Gelatin brand protein solution (available from Sigma) diluted with phosphate buffered saline ("PBS"). The gelatin is diluted 1:10 to 0.2% in sterile PBS at 37° C., and then 50 uL of the diluted gelatin solution is added to each well and incubated at room temperature for 30 minutes. Excess liquid is removed by aspiration without touching the wells and the surface is allowed to dry for at least 2 hours.

Exposing Cells to a Stressor or Test Agent

The cells may be exposed to a stressor or test agent by any suitable means known in the art. In some embodiments, the cells may be exposed to the stressor prior to placing the cells in the instrument that will be used to detect the metabolic parameter. For example, the cells may be exposed to UV radiation using a BIO-SUN brand solar simulator (available from Vilber Lourmat, France) prior to placing the cells in an XF Extracellular Flux Analyzer. In this example, the test medium may be removed from plate wells and replaced with 100 uL of PBS to reduce any undesirable effects the test medium may have on the UV radiation (e.g., absorbance or reflectance). In embodiments where a metabolic indicator will not detected within a suitable time after exposure (e.g., when obtaining a 24-hour measurement), the PBS may be replaced with the appropriate medium (e.g., the keratinocyte or fibroblast medium described above) immediately after exposure to the stressor but prior to placing the cells in an incubator. In order to obtain data from non-irradiated cells, the portion of the plate that will contain the non-irradiated cells may be covered with a UV impervious material such as aluminum foil. In some instances, a stressor and/or a test agent may be introduced into the test vessel before and/or after the cells are placed in the test device. For example, the test device may include one or more injector ports that enable the introduction of a substance directly into the test vessel before, during and/or after testing.

Measurement of Oxidative Phosphorylation and Glycolysis Metabolic Indicators

Oxygen consumption rate and extracellular acidification rate may be detected using an XF Extracellular Flux Analyzer or equivalent. The device should be capable of non-lethally and simultaneously detecting metabolic indicators of the oxphos and glycolysis pathways in a controlled environment, as well as providing kintetic data. The cells may be provided in a multi-well plate suitable for use with the instrument (e.g., 24-well or 96 well plate) and washed prior to testing. The cells may be washed by any suitable means known in the art (e.g., using a Seahorse Biosciences XF prep station). It may be desirable to use a suitable prep station such as an XF prep station available from Seahorse Biosciences). When washing the cells, it may be desirable to remove the medium from the wells and wash the cells three times with a suitable amount of test medium (e.g., 180 µL in a 96-well plate or 600 µL in a 24-well plate). After washing the cells, a suitable amount (e.g., 180 µL) of an appropriate test medium is placed in each well, and the cells are equilibrated at 37° C. in a $CO_2$-free incubator for 1-1.5 hours prior to taking placing the plate in the instrument for testing. Following the equilibration period, load the plate containing the cells into the instrument and equilibrate according to manufacturer's instructions. The entire test is conducted at 37° C. In some embodiments, the instrument may be to provide a three minute mix cycle, a two minute wait cycle, and a 3 minute measurement cycle for keratinocytes and a two minute mix cycle, two minute wait cycle, and 3 minute measurement cycle for fibroblasts. The cycles should be repeated for at least 88 minutes. It is to be appreciated that the cycles and times may be modified according to cell type and experiment design, as desired.

Example

The following example illustrates how the method herein can be used to identify synergistic combinations of skin care actives. Hydrogen peroxide is a well known ROS, and is used in this example to illustrate the undesirable metabolic effects associated with exposure of a cell to an oxidative stressor. The hydrogen peroxide was prepared at 10× working concentration in the fibroblast test medium described above. The test agents are niacinamide (also known as vitamin $B_3$) and tocoquinone both commercially available from Sigma. The test agents were each prepared at 10× the final working concentration in the fibroblast test medium described above to provide a test agent solution. The stressor solution and the test agent solutions were both warmed to 37° C. and pH adjusted to 7.4. The cells are frozen, human, dermal fibroblasts obtained from ATCC (BJ cell line). The cells were cultured and prepared according to the test method described above. The fibroblasts were plated in Gelatin-coated, 96-well plate. Each well contained approximately $4 \times 10^4$ cells and 180 µL of fibroblast test medium (i.e., Seahorse Biosciences DMEM, 25 mM glucose and 1 mM pyruvate) at 37° C. and pH 7.4.

An XF Extracellular Flux Analyzer was used to detect the metabolic indicators corresponding to the glycolysis and oxphos metabolic pathways (i.e., extracellular acidification rate and oxygen consumption rate). The 96-well plate was loaded into the analyzer and equilibrated according to the manufacturer's instructions. The test agents and stressor were each loaded into an automated injection port of the XF cartridge plate. The analyzer was programmed to sequentially run a two minute mix cycle and a 4 minute measurement cycle continuously for at least 108 minutes. Data points were collected and recorded by the analyzer. The analyzer was allowed to complete three cycles prior to the addition of the stressor solution or test agent solutions to provide a basal value for each metabolic indicator. After the third cycle was completed (i.e., about 18 minutes after detection began), the stressor and test agents were added to the wells from the appropriate injection port. The stressor solution was added to the well in sufficient amount to provide 1.5 mM hydrogen peroxide in the well. The test agents were added in sufficient amount to provide 0.25 mM niacinamide and 0.025 mM tocoquinone in the well. Eight wells in the 96-well plate were used as a control. The control the fibroblasts and fibroblast medium but was not contacted with hydrogen peroxide or either test agent. The fibroblasts were subjected to four test conditions. Each test condition used 8 wells of the 96-well plate. In the first test condition, the fibroblasts were contacted with the only 1.5 mM hydrogen peroxide. In the second test condition, the fibroblasts were with 0.25 mM niacinamide and 1.5 mM hydrogen peroxide in combination. In the third test condition, the fibroblasts were contacted with 0.025 mM tocoquinone and 1.5 mM hydrogen peroxide in combination. In the fourth test condition, the fibroblasts were contacted with 0.25 niacinamide, 0.025 mM tocoquinone and 1.5 mM hydrogen peroxide in combination. The results are illustrated in Table 1 and Table 2 below and FIGS. 9 and 10.

TABLE 1

Glycolysis

Average ECAR value per treatment group (percentage of rate 3)

| Rate number (time point) | Control | 1.5 mM hydrogen peroxide | 0.25 mM niacinamide + 1.5 mM hydrogen peroxide | 0.025 mM tocoquinone + 1.5 mM hydrogen peroxide | 0.25 mM niacinamide + 0.025 mM tocoquinone + 1.5 mM hydrogen peroxide |
|---|---|---|---|---|---|
| 1 | 110.46 | 101.82 | 107.35 | 107.45 | 103.25 |
| 2 | 101.32 | 100.66 | 99.41 | 99.58 | 100.64 |
| 3 | 100 | 100 | 100 | 100 | 100 |
| 4 | 120.82 | 48.46 | 64.35 | 56.77 | 58.78 |
| 5 | 108.27 | 29.55 | 33.18 | 35.13 | 35.31 |
| 6 | 110.45 | 33.64 | 34.48 | 32.57 | 32.69 |
| 7 | 111.48 | 37.41 | 42.19 | 32.46 | 32.29 |
| 8 | 112.20 | 28.20 | 49.60 | 34.54 | 34.67 |
| 9 | 111.60 | 17.74 | 55.87 | 36.55 | 38.49 |
| 10 | 110.74 | 15.41 | 60.52 | 36.68 | 42.70 |
| 11 | 110.90 | 14.87 | 62.89 | 35.75 | 47.52 |
| 12 | 112.18 | 13.82 | 60.57 | 32.86 | 55.00 |
| 13 | 113.44 | 13.32 | 57.46 | 29.78 | 58.82 |
| 14 | 114.71 | 12.78 | 55.04 | 28.15 | 59.70 |
| 15 | 115.79 | 11.82 | 52.85 | 28.07 | 61.66 |
| 16 | 117.40 | 11.52 | 51.52 | 30.73 | 65.94 |
| 17 | 118.38 | 11.36 | 49.85 | 31.49 | 69.54 |
| 18 | 118.98 | 11.57 | 47.58 | 31.18 | 70.74 |

Figure 9:
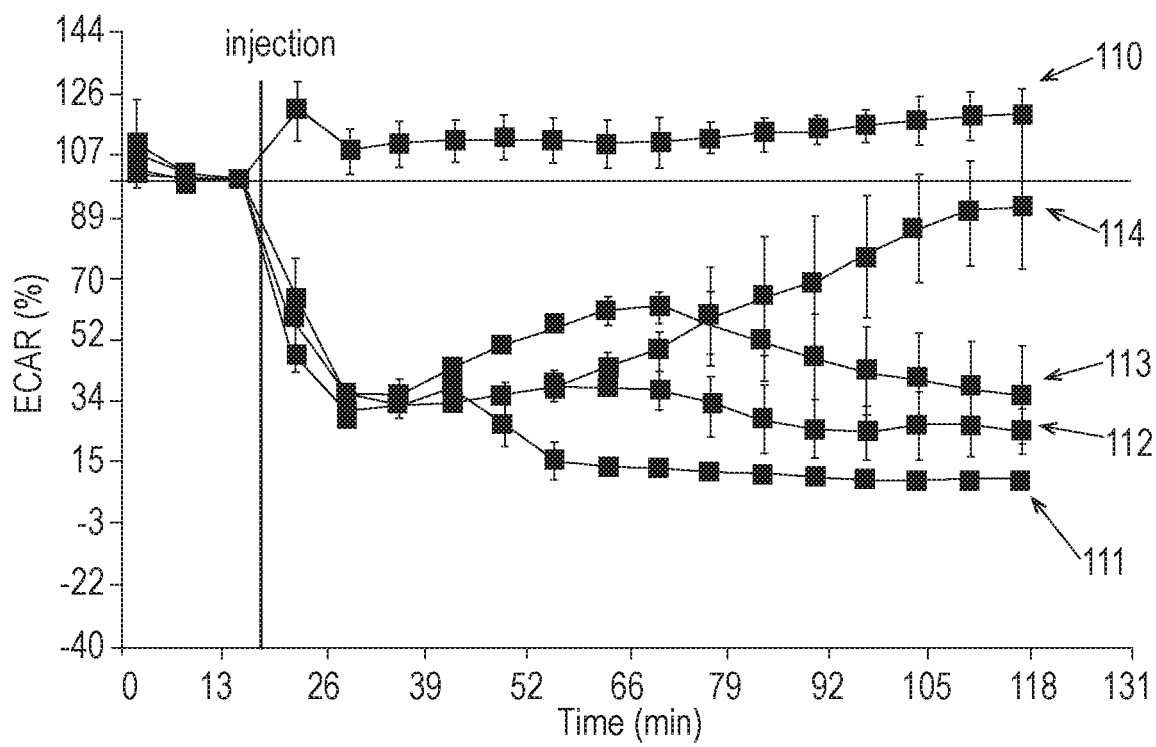
FIG. 9 is an illustration of the extracellular acidification rate of fibroblasts.

Table 1 illustrates the effects of hydrogen peroxide, niacinamide and tocoquinone, alone and in combination, on the acidification rate of the extracellular environment of fibroblasts. The data from Table 1 was analyzed via XF Software Version 1.8 to calculate the averages for each treatment group at each time point and compared to the change from baseline as a percentage that is represented graphically in FIG. 9. As discussed above, the first three measurements were made prior to the addition of the stressor or test agents to provide a basal value. FIG. 9 provides a plot for each of the control 110, 1.5 mM H$_2$O$_2$ alone 111, 0.25 mM niacinamide and 1.5 mM H$_2$O$_2$ in combination 113, 0.025 mM tocoquinone and 1.5 mM hydrogen peroxide in combination 112, and 0.25 mM niacinamide, 0.025 mM tocoquinone and 1.5 mM hydrogen peroxide in combination 114. As illustrated in Table 1 and FIG. 9, the 1.5 mM hydrogen peroxide by itself appears to causes a substantial decrease in extracellular acidification rate. After the sharp drop, the acidification rate continues to decrease until eventually it falls below the basal value approximately 40 minutes after addition of the hydrogen peroxide. Thus, a reasonable conclusion may be drawn that hydrogen peroxide causes a decrease in the glycolysis metabolism in human fibroblasts. Niacinamide, when added by itself at 0.25 mM, appears to cause an initial decrease in acidification rate before returning to the basal level or slightly above within about 20 minutes after its addition to the well. From this, a reasonable conclusion can be drawn that 0.25 mM niacinamide does not significantly affect glycolysis metabolism. However, when added in combination with hydrogen peroxide, niacinamide appears to lessen the detrimental effect of the hydrogen peroxide on glycolysis metabolism. That is, both the 0.1 mM and 0.25 mM niacinamide concentrations appear to slow the decrease in acidification rate and prevent the acidification rate from falling as far below the basal level when hydrogen peroxide is added alone.

TABLE 2

Oxidative Phosphorylation

Average OCR value per treatment group

| Rate number (time point) | Control | 1.5 mM hydrogen peroxide | 0.25 mM niacianamide + 1.5 mM hydrogen peroxide | 0.025 mM tocoquinone + 1.5 mM hydrogen peroxide | 0.25 mM niacinamide + 0.025 mM tocoquinone + 1.5 mM hydrogen peroxide |
|---|---|---|---|---|---|
| 1 | 99.67 | 97.05 | 99.16 | 101.04 | 99.17 |
| 2 | 101.37 | 99.80 | 101.76 | 101.44 | 102.02 |
| 3 | 100 | 100 | 100 | 100 | 100 |
| 4 | 88.75 | −139.75 | −21.15 | −21.48 | 38.28 |
| 5 | 93.67 | −4.58 | 63.31 | 64.55 | 106.15 |
| 6 | 94.26 | −6.07 | 60.15 | 68.43 | 103.02 |
| 7 | 93.874 | −24.10 | 47.41 | 59.47 | 89.81 |
| 8 | 93.35 | −34.10 | 38.52 | 53.35 | 79.85 |
| 9 | 92.32 | −44.54 | 34.85 | 49.83 | 75.55 |
| 10 | 91.57 | −53.81 | 32.39 | 48.18 | 72.23 |
| 11 | 90.66 | −58.25 | 31.10 | 48.82 | 69.38 |

TABLE 2-continued

Oxidative Phosphorylation

Average OCR value per treatment group

| Rate number (time point) | Control | 1.5 mM hydrogen peroxide | 0.25 mM niacianamide + 1.5 mM hydrogen peroxide | 0.025 mM tocoquinone + 1.5 mM hydrogen peroxide | 0.25 mM niacinamide + 0.025 mM tocoquinone + 1.5 mM hydrogen peroxide |
|---|---|---|---|---|---|
| 12 | 89.49 | −63.85 | 32.43 | 49.81 | 70.67 |
| 13 | 88.58 | −70.69 | 30.49 | 47.50 | 70.85 |
| 14 | 87.63 | −73.38 | 29.48 | 44.97 | 70.80 |
| 15 | 86.72 | −76.46 | 28.18 | 41.00 | 71.42 |
| 16 | 86.37 | −76.97 | 26.95 | 37.55 | 71.60 |
| 17 | 85.64 | −76.26 | 25.83 | 32.67 | 72.94 |
| 18 | 84.88 | −76.76 | 23.41 | 28.15 | 72.89 |

Figure 10:
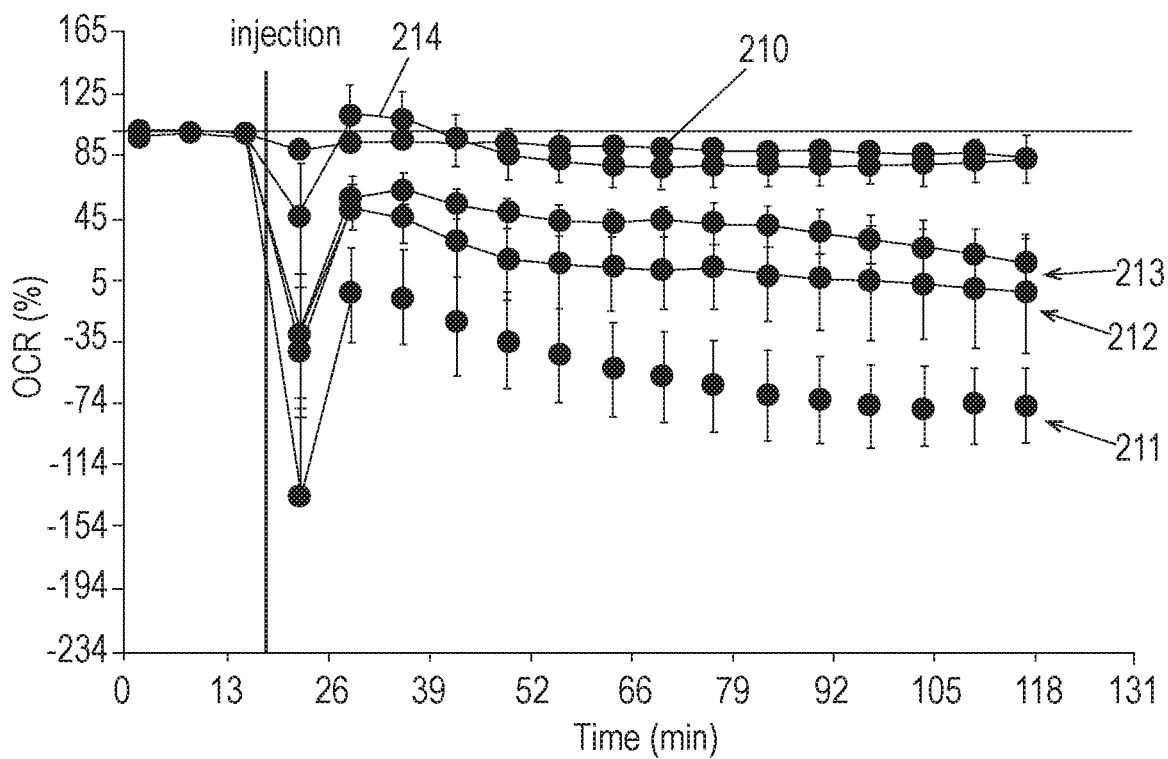
FIG. 10 is an illustration of the oxygen consumption rate of fibroblasts.

Table 2 illustrates the effects of hydrogen peroxide, niacinamide and tocoquinone, alone and in combination, on the oxygen consumption rate of fibroblasts. The data from Table 2 was analyzed via XF Software Version 1.8 to calculate the averages for each treatment group at each time point and compared to the change from baseline as a percentage that is represented graphically in FIG. 10. As discussed above, the first three measurements were made prior to the addition of the stressor or test agents to provide a basal value. FIG. 10 provides a plot for each of the control 210, 1.5 mM $H_2O_2$ alone 211, 0.25 mM niacinamide and 1.5 mM $H_2O_2$ in combination 213, 0.025 mM tocoquinone and 1.5 mM $H_2O_2$ in combination 212, and 0.25 mM niacinamide, 0.025 mM tocoquinone and 1.5 mM hydrogen peroxide in combination 214. As illustrated in Table 2 and FIG. 10, 1.5 mM $H_2O_2$ by itself initially causes a relatively sharp decrease in OCR followed by a less rapid increase. About 20 minutes or so after adding the hydrogen peroxide, the OCR began to approach a relatively constant rate, which is much lower than the basal rate. Thus, a reasonable conclusion may be drawn that hydrogen peroxide causes a decrease in the oxphos metabolism of human fibroblasts. As illustrated in FIG. 10, the niacinamide, when added at 0.25 mM in combination with the $H_2O_2$, generally tracks the shape of the hydrogen peroxide plot 211, but appears to lessen the reduction in OCR caused by the hydrogen peroxide. The response from tocoquinone, when added at 0.025 mM in combination with the $H_2O_2$, appears to lessen the reduction in OCR caused by the hydrogen peroxide about the same or slightly less than the niacinamide. It is important to note that neither the niacinamide nor the tocoquinone in this example, when combined individually with the $H_2O_2$, were able to bring the OCR of the fibroblasts back up to the basal value. Surprisingly, as illustrated in FIG. 10, when the niacinamide and tocoquinone are both used in combination with the $H_2O_2$, the OCR of the fibroblasts is brought back to about the basal value. Thus, in this example, the combination of niacinamide and tocoquinone provides a synergistic response to the reduction in oxphos metabolism of fibroblasts caused by hydrogen peroxide.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. In particular, U.S. Provisional Application Ser. Nos. 61/711,500 and 61/711,521 are incorporated herein by reference in their entirety. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An in vitro method of identifying or evaluating a synergistic combination of skin-care actives, comprising:
   (a) providing a first test vessel comprising a first type of cells disposed in a first medium and a second test vessel comprising a second type of cells disposed in a second medium, wherein the first and second types of cells are different types of cells;
   (b) providing a basal value for each of glycolysis and oxidative phosphorylation for the first type of cells and the second type of cells;
   (c) contacting the first and second types of cells with a first test agent and a second test agent in combination;
   (d) non-lethally detecting a metabolic indicator associated with each of glycolysis and oxidative phosphorylation in the first and second types of cells to provide a response of each metabolic pathway to the first and second test agents in combination; and
   (e) identifying the combination of the first and second test agents as a synergistic combination of skin-care actives when at least one of the responses indicates a synergistic increase over the corresponding basal values.

2. The method of claim 1, further comprising exposing the first and second types of cells to an oxidative stressor or reactive oxygen species (ROS).

3. The method of claim 2, wherein the cells are exposed to the oxidative stressor or ROS prior to contacting the cells with the test agents.

4. The method of claim 1, wherein one of the first and second types of cells are selected from the group consisting of keratinocytes and fibroblasts.

5. The method of claim 1, wherein detection of the metabolic indicators is done in an environment that prevents contact of the cells by undesirable contaminants.

6. The method of claim 1, wherein the metabolic indicator associated with the oxidative phosphorylation pathway is detected by measuring at least one of oxygen consumption rate and carbon dioxide generation rate.

7. The method of claim 1, wherein the metabolic indicator associated with the glycolysis pathway is detected by measuring at least one of extracellular acidification rate, extracellular lactic acid rate and lactate concentration rate.

* * * * *